(12) United States Patent
Marchenko et al.

(10) Patent No.: US 8,003,368 B2
(45) Date of Patent: Aug. 23, 2011

(54) METHOD FOR PRODUCING L-AMINO ACIDS BY FERMENTATION USING BACTERIA HAVING ENHANCED EXPRESSION OF XYLOSE UTILIZATION GENES

(75) Inventors: Aleksey Nikolaevich Marchenko, Moscow (RU); Sergey Vladimirovich Benevolensky, Moscow (RU); Elena Vitalievna Klyachko, Moscow (RU); Yuri Ivanovich Kozlov, Moscow (RU); Elvira Borisovna Voroshilova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/349,743

(22) Filed: Jan. 7, 2009

(65) Prior Publication Data

US 2009/0117623 A1    May 7, 2009

Related U.S. Application Data

(62) Division of application No. 11/079,392, filed on Mar. 15, 2005.

(60) Provisional application No. 60/610,545, filed on Sep. 17, 2004.

(30) Foreign Application Priority Data

Mar. 16, 2004 (RU) ................................ 2004107548
Mar. 14, 2005 (RU) ................................ 2005106720

(51) Int. Cl.
C12N 1/21       (2006.01)
C12N 1/20       (2006.01)
C12N 15/70      (2006.01)
C12N 9/00       (2006.01)
C12P 13/04      (2006.01)
C12P 13/24      (2006.01)
C07H 21/04      (2006.01)
C12P 13/14      (2006.01)
C12P 13/20      (2006.01)
C12P 13/08      (2006.01)

(52) U.S. Cl. ............... 435/252.33; 435/252.3; 435/69.1; 435/320.1; 435/106; 435/107; 435/108; 435/110; 435/115; 536/23.2

(58) Field of Classification Search .................. None
See application file for complete search history.

(56) References Cited

U.S. PATENT DOCUMENTS

| | | | |
|---|---|---|---|
| 4,970,157 A | 11/1990 | Hibino et al. | |
| 5,015,582 A | 5/1991 | Hibino et al. | |
| 5,175,107 A | 12/1992 | Debabov et al. | |
| 5,514,583 A | 5/1996 | Picataggio et al. | |
| 5,538,873 A | 7/1996 | Debabov et al. | |
| 5,573,945 A | 11/1996 | Ono et al. | |
| 5,631,157 A | 5/1997 | Debabov et al. | |
| 5,705,371 A | 1/1998 | Debabov et al. | |
| 5,712,133 A | 1/1998 | Picataggio et al. | |
| 5,726,053 A | 3/1998 | Picataggio et al. | |
| 5,843,760 A | 12/1998 | Zhang et al. | |
| 5,976,843 A | 11/1999 | Debabov et al. | |
| 6,165,756 A | 12/2000 | Debabov et al. | |
| 6,297,031 B1 | 10/2001 | Debabov et al. | |
| 6,303,348 B1 | 10/2001 | Livshits et al. | |
| 6,979,560 B1 | 12/2005 | Livshits et al. | |
| 7,091,014 B1 * | 8/2006 | Aristidou et al. | 435/161 |
| 7,399,617 B1 | 7/2008 | Livshits et al. | |
| 7,524,656 B2 | 4/2009 | Livshits et al. | |
| 7,527,950 B2 | 5/2009 | Livshits et al. | |
| 2001/0049129 A1 | 12/2001 | Debabov et al. | |
| 2002/0058314 A1 | 5/2002 | Livshits et al. | |
| 2002/0102670 A1 | 8/2002 | Livshits et al. | |
| 2004/0229321 A1 * | 11/2004 | Savrasova et al. | 435/106 |
| 2005/0239177 A1 | 10/2005 | Livshits et al. | |
| 2006/0014258 A1 | 1/2006 | Livshits et al. | |
| 2006/0040364 A1 | 2/2006 | Livshits et al. | |

FOREIGN PATENT DOCUMENTS

| | | |
|---|---|---|
| JP | 60-047692 | 3/1985 |
| JP | 63-157986 | 6/1988 |
| JP | 3-501682 | 4/1991 |
| JP | 2000-116390 | 4/2000 |
| JP | 2000-189177 | 7/2000 |
| RU | 2 175 351 | 10/2001 |

OTHER PUBLICATIONS

Song et al. Organization and regulation of the D-xylose operons in *Escherichia coli* K-12: XylR acts as a transcriptional activator. J Bacteriol. Nov. 1997;179(22):7025-32.*
Blattner et al. The complete genome sequence of *Escherichia coli* K-12, Science. Sep. 5, 1997; 277(5331): 1453-62.*
U.S. Appl. No. 11/830,961, filed Jul. 31, 2007, Filippov et al.
U.S. Appl. No. 11/830,969, filed Jul. 31, 2007, Gulevich et al.
U.S. Appl. No. 11/849,403, filed Sep. 4, 2007, Rybak et al.
U.S. Appl. No. 11/849,415, filed Sep. 4, 2007, Filippov et al.
U.S. Appl. No. 11/934,890, filed Nov. 5, 2007, Filippov et al.
U.S. Appl. No. 11/952,297, filed Dec. 7, 2007, Rybak et al.

(Continued)

*Primary Examiner* — Robert Mondesi
*Assistant Examiner* — Iqbal H Chowdhury
(74) *Attorney, Agent, or Firm* — Shelly Guest Cermak Cermak Nakajima LLP

(57) ABSTRACT

A method for producing an L-amino acid, such as L-histidine, L-threonine, L-lysine, L-glutamic acid, and L-tryptophan, using bacterium belonging to the genus *Escherichia* which has increased expression of genes, such as those of the xylABFGHR locus, which encode the xylose utilization enzymes, is disclosed. The method includes cultivating the L-amino acid producing bacterium in a culture medium containing xylose, and collecting the L-amino acid from the culture medium.

17 Claims, 1 Drawing Sheet

OTHER PUBLICATIONS

U.S. Appl. No. 12/017,379, filed Jan. 22, 2008, Rybak et al.
U.S. Appl. No. 12/022,299, filed Jan. 30, 2008, Rybak et al.
U.S. Appl. No. 12/031,757, filed Feb. 15, 2008, Klyachko et al.
U.S. Appl. No. 61/031,834, filed Feb. 27, 2008, Samsonov et al.
U.S. Appl. No. 61/053,704, filed May 16, 2008, Rybak et al.
U.S. Appl. No. 12/125,988, filed May 23, 2008, Filippov et al.
U.S. Appl. No. 12/212,743, filed Sep. 18, 2008, Rybak et al.
U.S. Appl. No. 12/238,704, filed Sep. 26, 2008, Shakulov et al.
U.S. Appl. No. 12/253,415, filed Oct. 17, 2008, Filippov et al.
U.S. Appl. No. 12/275,842, filed Nov. 21, 2008, Rybak et al.
U.S. Appl. No. 12/323,893, filed Nov. 26, 2008, Filippov et al.
U.S. Appl. No. 12/345,971, filed Dec. 30, 2008, Filippov et al.

* cited by examiner

METHOD FOR PRODUCING L-AMINO ACIDS BY FERMENTATION USING BACTERIA HAVING ENHANCED EXPRESSION OF XYLOSE UTILIZATION GENES

This application is a divisional application under 35 U.S.C. §120 of U.S. patent application Ser. No. 11/079,392, filed on Mar. 15, 2005, which claims the benefit 35 USC §119 of U.S. Provisional Patent Application No. 60/610,545, filed on Sep. 17, 2004, U.S. patent application Ser. No. 11/059,686, filed on Feb. 17, 2005, Russian Patent Application No. 2005106720, filed on Mar. 14, 2005, and Russian Patent Application No. 2004107548, filed on Mar. 16, 2004, all of which are incorporated by reference. The Sequence Listing in electronic format filed herewith is also hereby incorporated by reference in its entirety (File Name: US-161D_Seq_List; File Size: 57 KB; Date Created: Jan. 7, 2009).

BACKGROUND OF THE INVENTION

1. Field of the Invention

The present invention relates to a method for producing L-amino acids by pentose fermentation, and more specifically to a method for producing L-amino acids using bacteria having enhanced expression of xylose utilization genes by fermentation of mixture of arabinose and/or xylose along with glucose as a carbon source. The non-expensive carbon source which includes a mixture of hexoses and pentoses of hemicellulose fractions from cellulosic biomass can be utilized for commercial production of L-amino acids, for example, L-histidine, L-threonine, L-lysine, L-glutamic acid, and L-tryptophan.

2. Brief Description of the Related Art

Conventionally, L-amino acids have been industrially produced by fermentation processes using strains of different microorganisms. The fermentation media for the process typically contains sufficient amounts of different sources of carbon and nitrogen.

Traditionally, various carbohydrates such as hexoses, pentoses, trioses; various organic acids and alcohols are used as a carbon source. Hexoses include glucose, fructose, mannose, sorbose, galactose and the like. Pentoses include arabinose, xylose, ribose and the like. However, the above-mentioned carbohydrates and other traditional carbon sources, such as molasses, corn, sugarcane, starch, its hydrolysate, etc., currently used in industry are rather expensive. Therefore, finding alternative less expensive sources for production of L-amino acids is desirable.

Cellulosic biomass is a favorable feedstock for L-amino acid production because it is both readily available and less expensive than carbohydrates, corn, sugarcane or other sources of carbon. Typical amounts of cellulose, hemicellulose and lignin in biomass are approximately 40-60% of cellulose, 20-40% of hemicellulose 10-25% of lignin and 10% of other components. The cellulose fraction consists of polymers of a hexose sugar, typically glucose. The hemicellulose fraction is made up of mostly pentose sugars, including xylose and arabinose. The composition of various biomass feedstocks is shown in Table 1.

TABLE 1

| Material | Six-carbon sugars | Five-carbon sugars | Lignin | Ash |
| --- | --- | --- | --- | --- |
| Hardwoods | 39-50% | 18-28% | 15-28% | 0.3-1.0% |
| Softwoods | 41-57% | 8-12% | 24-27% | 0.1-0.4% |

More detailed information about composition of over 150 biomass samples is summarized in the "Biomass Feedstock Composition and Property Database".

An industrial process for effective conversion of cellulosic biomass into usable fermentation feedstock, typically a mixture of carbohydrates, is expected to be developed in the near future. Therefore, utilization of renewable energy sources such as cellulose and hemicellulose for production of useful compounds is expected to increase in the near future (Aristidou A., Pentila. M., Curr. Opin. Biotechnol, 2000, April, 11:2, 187-198). However, a great majority of published articles and patents, or patent applications, describe the utilization of cellulosic biomass by biocatalysts (bacteria and yeasts) for production of ethanol, which is expected to be useful as an alternative fuel. Such processes include fermentation of cellulosic biomass using different modified strains of *Zymomonas mobilis* (Deanda K. et al, Appl. Environ. Microbiol., 1996 Dec., 62:12, 4465-70; Mohagheghi A. et al, Appl. Biochem. Biotechnol., 2002, 98-100:885-98; Lawford H. G., Rousseau J. D., Appl. Biochem. Biotechnol, 2002, 98-100:429-48; PCT applications WO95/28476, WO98/50524), modified strains of *Escherichia coli* (Dien B. S. et al, Appl. Biochem. Biotechnol, 2000, 84-86:181-96; Nichols N. N. et al, Appl. Microbiol. Biotechnol., 2001 July, 56:1-2, 120-5; U.S. Pat. No. 5,000,000). Xylitol can be produced by fermentation of xylose from hemicellulosic sugars using *Candida tropicalis* (Walthers T. et al, Appl. Biochem. Biotechnol., 2001, 91-93: 423-35). 1,2-propanediol can be produced by fermentation of arabinose, fructose, galactose, glucose, lactose, maltose, sucrose, xylose, and combination thereof using recombinant *Escherichia coli* strain (U.S. Pat. No. 6,303,352). Also, it has been shown that 3-dehydroshikimic acid can be obtained by fermentation of a glucose/xylose/arabinose mixture using *Escherichia coli* strain. The highest concentrations and yields of 3-dehydroshikimic acid were obtained when the glucose/xylose/arabinose mixture was used as the carbon source, as compared to when either xylose or glucose alone was used as a carbon source (Kai Li and J. W. Frost, Biotechnol. Prog., 1999, 15, 876-883).

It is has been reported that *Escherichia coli* can utilize pentoses such as L-arabinose and D-xylose (*Escherichia coli* and *Salmonella*, Second Edition, Editor in Chief: F. C. Neidhardt, ASM Press, Washington D.C., 1996). Transport of L-arabinose into the cell is performed by two inducible systems: (1) a low-affinity permease ($K_m$ about 0.1 mM) encoded by araE gene, and (2) a high-affinity ($K_m$ 1 to 3 μM) system encoded by the araFG operon. The araF gene encodes a periplasmic binding protein (306 amino acids) with chemotactic receptor function, and the araG locus encodes an inner membrane protein. The sugar is metabolized by a set of enzymes encoded by the araBAD operon: an isomerase (encoded by the araA gene), which reversibly converts the aldose to L-ribulose; a kinase (encoded by the araB gene), which phosphorylates the ketose to L-ribulose 5-phosphate; and L-ribulose-5-phosphate-4-epimerase (encoded by the araD gene), which catalyzes the formation of D-xylose-5-phosphate (*Escherichia coli* and *Salmonella*, Second Edition, Editor in Chief: F. C. Neidhardt, ASM Press, Washington D.C., 1996).

Most strains of *E. coli* grow on D-xylose, but a mutation is necessary for the K-12 strain to grow on the compound. Utilization of this pentose is through an inducible and catabolite-repressible pathway involving transport across the cytoplasmic membrane by two inducible permeases (not active on D-ribose or D-arabinose), isomerization to D-xylulose, and ATP-dependent phosphorylation of the pentulose to yield D-xylulose 5-phosphate. The high-affinity ($K_m$ 0.3 to 3 μM) transport system depends on a periplasmic binding protein (37,000 Da) and is probably driven by a high-energy compound. The low-affinity ($K_m$ about 170 μM) system is energized by a proton motive force. This D-xylose-proton-symport system is encoded by the xylE gene. The main gene cluster specifying D-xylose utilization is xylAB(RT). The xylA gene encodes the isomerase (54,000 Da) and xylB gene encodes the kinase (52,000 Da). The operon contains two transcriptional start points, with one of them being inserted upstream of the xylB open reading frame. Since the low-affinity permease is specified by the unlinked xylE, the xylT locus, also named as xylF (xylFGHR), probably codes for the high-affinity transport system and therefore should contain at least two genes (one for a periplasmic protein and one for an integral membrane protein) (*Escherichia coli* and *Salmonella*, Second Edition, Editor in Chief: F. C. Neidhardt, ASM Press, Washington D.C., 1996). The xylFGH genes code for xylose ABC transporters, where xylF gene encodes the putative xylose binding protein, xylG gene encodes the putative ATP-binding protein, xylH gene encodes the putative membrane component, and xylR gene encodes the xylose transcriptional activator.

Introduction of the above-mentioned *E. coli* genes which code for L-arabinose isomerase, L-ribulokinase, L-ribulose 5-phosphate 4-epimerase, xylose isomerase and xylulokinase, in addition to transaldolase and transketolase, allow a microbe, such as *Zymomonas mobilis*, to metabolize arabinose and xylose to ethanol (WO/9528476, WO98/50524). In contrast, *Zymomonas* genes which code for alcohol dehydrogenase (ADH) and pyruvate decarboxylase (PDH) are useful for ethanol production by *Escherichia coli* strains (Dien B. S. et al, Appl. Biochem. Biotechnol, 2000, 84-86:181-96; U.S. Pat. No. 5,000,000).

A process for producing L-amino acids, such as L-isoleucine, L-histidine, L-threonine and L-tryptophan, by fermentation of a mixture of glucose and pentoses, such as arabinose and xylose, was disclosed earlier by authors of the present invention (Russian patent application 2003105269).

However, at present, there are no reports describing bacteria having enhanced expression of the xylose utilization genes such as those at the xylABFGHR locus, or use of these genes for production of L-amino acids from a mixture of hexose and pentose sugars.

SUMMARY OF THE INVENTION

An object of present invention is to enhance production of an L-amino acid producing strain, to provide an L-amino acid producing bacterium having enhanced expression of xylose utilization genes, and to provide a method for producing L-amino acids from a mixture of hexose sugars, such as glucose, and pentose sugars, such as xylose or arabinose, using the bacterium. A fermentation feedstock obtained from cellulosic biomass may be used as a carbon source for the culture medium. This aim was achieved by finding that the xylABFGHR locus cloned on a low copy vector enhances production of L-amino acids, for example, L-histidine, L-threonine, L-lysine, L-glutamic acid and L-tryptophan. A microorganism is used which is capable of growth on the fermentation feedstock and is efficient in production of L-amino acids. The fermentation feedstock consists of xylose and arabinose along with glucose, as the carbon source. L-amino acid producing strains are exemplified by *Escherichia coli* strain. Thus the present invention has been completed.

It is an object of the present invention to provide an L-amino acid producing bacterium of the Enterobacteriaceae family which has an enhanced activity of any of the xylose utilization enzymes.

It is a further object of the present invention to provide the bacterium described above, wherein the bacterium belongs to the genus *Escherichia*.

It is a further object of the present invention to provide the bacterium described above, wherein the bacterium belongs to the genus *Pantoea*.

It is a further object of the present invention to provide the bacterium described above, wherein the activities of the xylose utilization enzymes are enhanced by increasing the expression amount of the xylABFGHR locus.

It is a further object of the present invention to provide the bacterium described above, wherein the activities of the xylose utilization enzymes are increased by increasing the copy number of the xylABFGHR locus or modifying an expression control sequence of the genes so that the expression of the genes are enhanced.

It is a further object of the present invention to provide the bacterium described above, wherein the copy number is increased by transforming the bacterium with a low copy vector harboring the xylABFGHR locus.

It is a further object of the present invention to provide the bacterium described above, wherein the xylABFGHR locus originates from a bacterium belonging to the genus *Escherichia*.

It is a further object of the present invention to provide a method for producing L-amino acids, which comprises cultivating the bacterium described above in a culture medium containing a mixture of glucose and pentose sugars, and collecting the L-amino acid from the culture medium.

It is a further object of the present invention to provide the method described above, wherein the pentose sugars are arabinose and xylose.

It is a further object of the present invention to provide the method described above, wherein the mixture of sugars is a feedstock mixture of sugars obtained from cellulosic biomass.

It is a further object of the present invention to provide the method described above, wherein the L-amino acid to be produced is L-histidine.

It is a further object of the present invention to provide the method described above, wherein the bacterium has enhanced expression of genes for L-histidine biosynthesis.

It is a further object of the present invention to provide the method described above, wherein the L-amino acid to be produced is L-threonine.

It is a further object of the present invention to provide the method described above, wherein the bacterium has enhanced expression of genes for L-threonine biosynthesis.

It is a further object of the present invention to provide the method described above, wherein the L-amino acid to be produced is L-lysine.

It is a further object of the present invention to provide the method described above, wherein the bacterium has enhanced expression of genes for L-lysine biosynthesis.

It is a further object of the present invention to provide the method described above, wherein the L-amino acid to be produced is L-glutamic acid.

It is a further object of the present invention to provide the method described above, wherein the bacterium has enhanced expression of genes for L-glutamic acid biosynthesis.

It is a further object of the present invention to provide the method described above, wherein the L-amino acid to be produced is L-tryptophan.

It is a further object of the present invention to provide the method described above, wherein the bacterium has enhanced expression of genes for L-tryptophan biosynthesis.

The method for producing L-amino acids includes production of L-histidine by fermentation of a mixture of glucose and pentose sugars, such as arabinose and xylose. Also, the method for producing L-amino acids includes production of L-threonine by fermentation of a mixture of glucose and pentose sugars, such as arabinose and xylose. Also, the method for producing L-amino acids includes production of L-lysine by fermentation of a mixture of glucose and pentose sugars, such as arabinose and xylose. Also, the method for producing L-amino acids includes production of L-glutamic acid by fermentation of a mixture of glucose and pentose sugars, such as arabinose and xylose. Also, the method for producing L-amino acids includes production of L-tryptophan by fermentation of a mixture of glucose and pentose sugars, such as arabinose and xylose. This mixture of glucose and pentose sugars used as a fermentation feedstock can be obtained from under-utilized sources of plant biomass, such as cellulosic biomass, preferably hydrolysate of cellulose.

DESCRIPTION OF THE PREFERRED EMBODIMENTS

Figure 1:
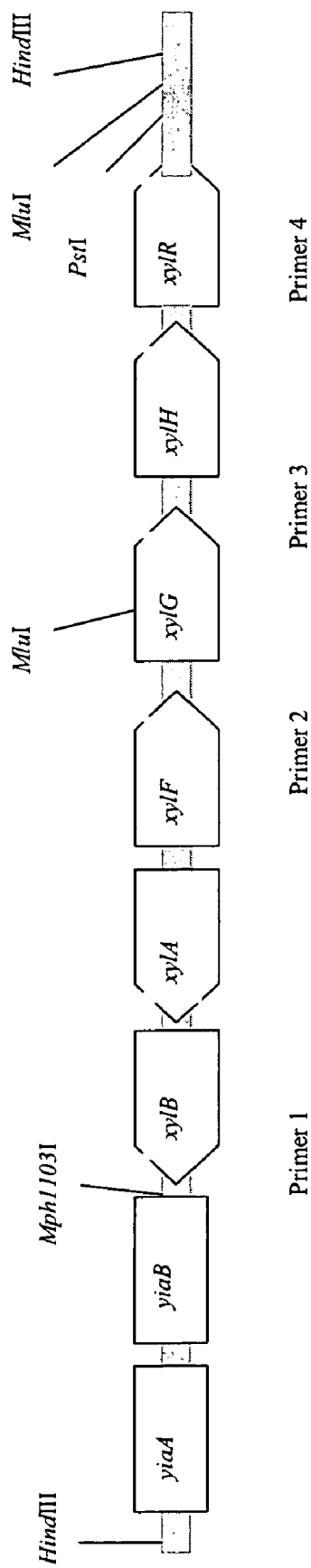
FIG. 1 shows the structure of the xylABFGHR locus on the chromosome of *E. Coli* strain MG1655. The arrows on the diagram indicate positions of primers used in PCR.

In the present invention, "L-amino acid producing bacterium" means a bacterium, which has an ability to cause accumulation of L-amino acids in a medium, when the bacterium of the present invention is cultured in the medium. The L-amino acid producing ability may be imparted or enhanced by breeding. The term "L-amino acid producing bacterium" used herein also means a bacterium which is able to produce and cause accumulation of L-amino acids in a culture medium in amounts larger than a wild-type or parental strain, and preferably means that the microorganism is able to produce and cause accumulation in a medium of an amount not less than 0.5 g/L, more preferably not less than 1.0 g/L of target L-amino acid. "L-amino acids" include L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine and L-valine.

The Enterobacteriaceae family includes bacteria belonging to the genera *Escherichia*, *Enterobacter*, *Erwinia*, *Klebsiella*, *Pantoea*, *Photorhabdus*, *Providencia*, *Salmonella*, *Serratia*, *Shigella*, *Morganella Yersinia*, etc. Specifically, those classified into the Enterobacteriaceae according to the taxonomy used in the NCBI (National Center for Biotechnology Information) database can be used. A bacterium belonging to the genus *Escherichia* or *Pantoea* are preferred.

The phrase "a bacterium belonging to the genus *Escherichia*" means that the bacterium is classified in the genus *Escherichia* according to the classification known to a person skilled in the art of microbiology. Examples of a bacterium belonging to the genus *Escherichia* as used in the present invention include, but are not limited to, *Escherichia coli* (*E. coli*).

The bacterium belonging to the genus *Escherichia* that can be used in the present invention is not particularly limited, however for example, bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans*, *Pantoea ananatis*, *Pantoea stewartii* or the like, based on nucleotide sequence analysis of 16S rRNA, etc.

The phrase "having enhanced activity of a xylose utilization enzyme" means that the activity of the enzyme per cell is higher than that of a non-modified strain, for example, a wild-type strain. Examples include where the number of enzyme molecules per cell increases, and where specific activity per enzyme molecule increases, and so forth. The amount of the protein encoded by the gene can be measured by known methods including SDS-PAGE followed by immunoblotting assay (Western blotting analysis) and the like. Furthermore, a wild-type strain that can act as a control includes, for example *Escherichia coli* K-12. As a result of enhancing the intracellular activity of a xylose utilization enzyme, accumulation of L-amino acids, such as L-histidine, L-threonine, L-lysine, L-glutamic acid, and/or L-tryptophan, in a medium is observed.

The "xylose utilization enzymes" include enzymes of xylose transport, xylose isomerization and xylose phosphorylation, and regulatory proteins. Such enzymes include xylose isomerase, xylulokinase, xylose transporters, and xylose transcriptional activator. Xylose isomerase catalyzes the reaction of isomerization of D-xylose to D-xylulose. Xylulokinase catalyzes the reaction of phosphorylation of D-xylulose using ATP yielding D-xylulose-5-phosphate and ADP. The presence of activity of xylose utilization enzymes, such as xylose isomerase, xylulokinase, is determined by complementation of corresponding xylose isomerase-negative or xylulokinase-negative *E. coli* mutants, respectively.

The phrase "a bacterium belonging to the genus *Escherichia*" means that the bacterium is classified as the genus *Escherichia* according to the classification known to a person skilled in the microbiology. An example of a microorganism belonging to the genus *Escherichia* as used in the present invention is *Escherichia coli* (*E. coli*).

The phrase "increasing the expression amount of gene(s)" means that the expression amount of gene(s) is higher than that of a non-modified strain, for example, a wild-type strain. Examples of such modification include increasing the number of expressed gene(s) per cell, increasing the expression level of the gene(s) and so forth. The quantity of the copy number of an expressed gene is measured, for example, by restricting the chromosomal DNA followed by Southern blotting using a probe based on the gene sequence, fluorescence in situ hybridization (FISH), and the like. The level of gene expression can be measured by various methods including Northern blotting, quantitative RT-PCR, and the like. Furthermore, a wild-type strain that can act as a control includes, for example *Escherichia coli* K-12. As a result of enhancing the intracellular activity of a xylose utilization enzyme, accumulation of L-amino acid, such as L-histidine, L-threonine, L-lysine, L-glutamic acid, or L-tryptophan, in a medium containing pentose sugar, such as xylose, is observed.

Enhancing the activities of xylose utilization enzymes in a bacterial cell can be attained by increasing the expression of genes which code for said enzymes. Genes of xylose utilization include any genes derived from bacteria of Enterobacteriaceae family, as well as genes derived from other bacteria such as thermophilic *Bacillus* sp. (Biochem. Mol. Bio. Int., 1996, 39(5), 1049-1062). Genes derived from bacteria belonging to the genus *Escherichia* are preferred.

The gene coding for xylose isomerase from *E. coli* (EC numbers 5.3.1.5) is known and has been designated xylA (nucleotide numbers 3727072 to 3728394 in the sequence of GenBank accession NC_000913.1, gi:16131436). The gene coding for xylulokinase (EC numbers 2.7.1.17) is known and has been designated xylB (nucleotide numbers 3725546 to 3727000 in the sequence of GenBank accession NC_000913.1, gi:16131435). The gene coding for xylose binding protein transport system is known and has been designated xylF (nucleotide numbers 3728760 to 3729752 in the sequence of GenBank accession NC_000913.1, gi: 16131437). The gene coding for putative ATP-binding protein of xylose transport system is known and has been designated xylG (nucleotide numbers 3729830 to 3731371 in the sequence of GenBank accession NC_000913.1, gi:16131438). The gene coding for the permease component of the ABC-type xylose transport system is known and has been designated xylH gene (nucleotide numbers 3731349 to 3732530 in the sequence of GenBank accession NC_000913.1, gi:16131439). The gene coding for the transcriptional regulator of the xyl operon is known and has been designated xylR (nucleotide numbers 3732608 to 3733786 in the sequence of GenBank accession NC_000913.1, gi:16131440). Therefore, the above-mentioned genes can be obtained by PCR (polymerase chain reaction; refer to White, T. J. et al., Trends Genet., 5, 185 (1989)) using primers based on the nucleotide sequence of the genes.

Genes coding for xylose utilization enzymes from other microorganisms can be similarly obtained.

The xylA gene from *Escherichia coli* is exemplified by a DNA which encodes the following protein (A) or (B):
(A) a protein having the amino acid sequence shown in SEQ ID NO:2; or
(B) a protein having an amino acid sequence which includes deletion, substitution, insertion or addition of one or several amino acids in the amino acid sequence shown in SEQ ID NO:2, and which has an activity of xylose isomerase.

The xylB gene from *Escherichia coli* is exemplified by a DNA which encodes the following protein (C) or (D):
(C) a protein having the amino acid sequence shown in SEQ ID NO: 4; or
(D) a protein having an amino acid sequence which includes deletion, substitution, insertion or addition of one or several amino acids in the amino acid sequence shown in SEQ ID NO:4, and which has an activity of xylulokinase.

The xylF gene from *Escherichia coli* is exemplified by a DNA which encodes the following protein (E) or (F):
(E) a protein having the amino acid sequence shown in SEQ ID NO:6; or
(F) a protein having an amino acid sequence which includes deletion, substitution, insertion or addition of one or several amino acids in the amino acid sequence shown in SEQ ID NO:6, and which has activity to increase the amount of L-amino acid, such as L-histidine, L-threonine, L-lysine, L-glutamic acid, or L-tryptophan, in a medium, when the amount of protein is increased in the L-amino acid producing bacterium along with the amount of proteins coded by xylAB and xylGHR genes.

The xylG gene from *Escherichia coli* is exemplified by a DNA which encodes the following protein (G) or (H):
(G) a protein having the amino acid sequence shown in SEQ ID NO:8; or
(H) a protein having an amino acid sequence which includes deletion, substitution, insertion or addition of one or several amino acids in the amino acid sequence shown in SEQ ID NO:8, and which has an activity to increase the amount of L-amino acid, such as L-histidine, L-threonine, L-lysine, L-glutamic acid, or L-tryptophan, in a medium, when the amount of protein is increased in the L-amino acid producing bacterium along with the amount of proteins coded by xylAB and xylFHR genes.

The xylH gene from *Escherichia coli* is exemplified by a DNA which encodes the following protein (I) or (J):
(I) a protein having the amino acid sequence shown in SEQ ID NO:10;
(J) a protein having an amino acid sequence including deletion, substitution, insertion or addition of one or several amino acids in the amino acid sequence shown in SEQ ID NO:10, and which has an activity to increase the amount of L-amino acid, such as L-histidine, L-threonine, L-lysine, L-glutamic acid, or L-tryptophan, in a medium, when the amount of protein is increased in the L-amino acid producing bacterium along with the amount of proteins coded by xylAB and xylFGR genes.

The xylR gene from *Escherichia coli* is exemplified by a DNA which encodes the following protein (K) or (L):
(K) a protein having the amino acid sequence shown in SEQ ID NO:12;
(L) a protein having an amino acid sequence including deletion, substitution, insertion or addition of one or several amino acids in the amino acid sequence shown in SEQ ID NO:12, and which has an activity to increase the amount of L-amino acid, such as L-histidine, L-threonine, L-lysine, L-glutamic acid, or L-tryptophan, in a medium, when the amount of protein is increased in the L-amino acid producing bacterium along with the amount of proteins coded by xylAB and xylFGH genes.

The DNA coding for xylose isomerase includes a DNA coding for the protein which includes deletion, substitution, insertion or addition of one or several amino acids in one or more positions on the protein (A) as long as the activity of the protein is not lost. Although the number of "several" amino acids differs depending on the position or the type of amino acid residues in the three-dimensional structure of the protein, it may be 2 to 50, preferably 2 to 20, and more preferably 2 to 10 for the protein (A). This is because some amino acids have high homology to one another and substitution of such an amino acid does not greatly affect the three dimensional structure of the protein and its activity. Therefore, the protein (B) may have homology of not less than 30 to 50%, preferably 50 to 70%, more preferably 70-90%, still more preferably more then 90% and most preferably more than 95% with respect to the entire amino acid sequence for xylose isomerase, and which has the activity of xylose isomerase. The same approach and homology determination can be applied to other proteins (C), (E), (G), (I) and (K).

To evaluate the degree of protein or DNA homology, several calculation methods such as BLAST search, FASTA search and ClustalW, can be used.

BLAST (Basic Local Alignment Search Tool) is the heuristic search algorithm employed by the programs blastp, blastn, blastx, megablast, tblastn, and tblastx; these programs ascribe significance to their findings using the statistical methods of Karlin, Samuel and Stephen F. Altschul ("Methods for assessing the statistical significance of molecular sequence features by using general scoring schemes". Proc. Natl. Acad. Sci. USA, 1990, 87:2264-68; "Applications and statistics for multiple high-scoring segments in molecular sequences". Proc. Natl. Acad. Sci. USA, 1993, 90:5873-7).

FASTA search method described by W. R. Pearson ("Rapid and Sensitive Sequence Comparison with FASTP and FASTA", Methods in Enzymology, 1990 183:63-98). ClustalW method described by Thompson J. D., Higgins D. G. and Gibson T. J. ("CLUSTAL W: improving the sensitivity of progressive multiple sequence alignment through sequence weighting, position-specific gap penalties and weight matrix choice", Nucleic Acids Res. 1994, 22:4673-4680).

Changes to the protein defined in (A) such as those described above are typically conservative changes so as to maintain the activity of the protein. Substitution changes include those in which at least one residue in the amino acid sequence has been removed and a different residue inserted in its place. Examples of amino acids which may be substituted for an original amino acid in the above protein and which are regarded as conservative substitutions include: Ala substituted with ser or thr; arg substituted with gln, his, or lys; asn substituted with glu, gln, lys, his, asp; asp substituted with asn, glu, or gln; cys substituted with ser or ala; gln substituted with asn, glu, lys, his, asp, or arg; glu substituted with asn, gln, lys, or asp; gly substituted with pro; his substituted with asn, lys, gln, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

The DNA coding for substantially the same protein as the protein defined in (A) may be obtained by, for example, modification of the nucleotide sequence coding for the protein defined in (A) using site-directed mutagenesis so that one or more amino acid residue will be deleted, substituted, inserted or added. Such modified DNA can be obtained by conventional methods using treatments with reagents and conditions generating mutations. Such treatments include treating the DNA coding for proteins of present invention with hydroxylamine or treating the bacterium harboring the DNA with UV irradiation or reagents such as N-methyl-N'-nitro-N-nitrosoguanidine or nitrous acid.

The DNA coding for the xylose isomerase includes variants which can be found in the different strains of bacteria belonging to the genus *Escherichia* due to natural diversity. The DNA coding for such variants can be obtained by isolating the DNA which hybridizes with the xylA gene or a part of the gene under the stringent conditions, and which codes for the protein having an activity of xylose isomerase. The phrase "stringent conditions" referred to herein include conditions under which a so-called specific hybrid is formed, and non-specific hybrid is not formed. For example, the stringent conditions include conditions under which DNAs having high homology, for instance DNAs having homology no less than 70%, preferably no less than 80%, more preferably no less than 90%, most preferably no less than 95% to each other, are hybridized. Alternatively, the stringent conditions are exemplified by conditions which comprise ordinary conditions of washing in Southern hybridization, e.g., 60° C., 1×SSC, 0.1% SDS, preferably 0.1×SSC, 0.1% SDS. Duration of the washing procedure depends on the type of membrane used for blotting and, as a rule, what is recommended by manufacturer. For example, recommended duration of washing the Hybond™ N+ nylon membrane (Amersham) under stringent conditions is 15 minutes. Preferably, washing may be performed 2 to 3 times. A partial sequence of the nucleotide sequence of SEQ ID NO: 1 can also be used as a probe for DNA that codes for variants and hybridizes with xylA gene. Such a probe may be prepared by PCR using oligonucleotides produced based on the nucleotide sequence of SEQ ID NO: 1 as primers, and a DNA fragment containing the nucleotide sequence of SEQ ID NO: 1 as a template. When a DNA fragment in a length of about 300 bp is used as the probe, the conditions of washing for the hybridization can be, for example, 50° C., 2×SSC, and 0.1% SDS.

DNAs coding for substantially the same proteins as the other enzymes of xylose utilization can be obtained by methods which are similar to those used to obtain xylose isomerase, as described above.

Transformation of a bacterium with a DNA coding for a protein means introduction of the DNA into a bacterium cell, for example, by conventional methods to increase expression of the gene coding for the protein of present invention and to enhance the activity of the protein in the bacterial cell.

The bacterium of the present invention also includes one where the activity of the protein of the present invention is enhanced by transformation of said bacterium with a DNA coding for a protein as defined in (A) or (B), (C) or (D), (E) or (F), (G) or (H), (I) or (J), and (K) or (L), or by alteration of expression regulation sequence of said DNA on the chromosome of the bacterium.

A method of the enhancing gene expression includes increasing the gene copy number. Introduction of a gene into a vector that is able to function in a bacterium belonging to the genus *Escherichia* increases copy number of the gene. For such purposes multi-copy vectors can be preferably used. Preferably, low copy vectors are used. The low-copy vector is exemplified by pSC101, pMW118, pMW119 and the like. The term "low copy vector" is used for vectors which have a copy number of up to 5 copies per cell. Methods of transformation include any method known to those with skill in the art. For example, a method of treating recipient cells with calcium chloride so as to increase permeability of the cells to DNA has been reported for *Escherichia coli* K-12 (Mandel, M. and Higa, A., J. Mol. Biol., 53, 159 (1970)) and may be used.

Enhancement of gene expression may also be achieved by introduction of multiple copies of the gene into a bacterial chromosome by, for example, a method of homologous recombination, Mu integration or the like. For example, one round of Mu integration allows introduction into a bacterial chromosome of up to 3 copies of the gene.

On the other hand, the enhancement of gene expression can be achieved by placing the DNA of the present invention under the control of a more potent promoter instead of the native promoter. The strength of a promoter is defined by the frequency of acts of RNA synthesis initiation. Methods for evaluation of the strength of a promoter and examples of potent promoters are described by Deuschle, U., Kammerer, W., Gentz, R., Bujard, H. (Promoters in *Escherichia coli*: a hierarchy of in vivo strength indicates alternate structures. EMBO J. 1986, 5, 2987-2994). For example, $P_R$ promoter is known as a potent constitutive promoter. Other known potent promoters are $P_L$ promoter, lac promoter, trp promoter, trc promoter, of lambda phage and the like.

The enhancement of translation can be achieved by introducing a more efficient Shine-Dalgarno sequence (SD sequence) into the DNA of the present invention instead of the native SD sequence. The SD sequence is a region upstream of the start codon of the mRNA which interacts with the 16S RNA of the ribosome (Shine J. and Dalgarno L., Proc. Natl. Acad. Sci. USA, 1974, 71, 4, 1342-6).

Use of a more potent promoter can be combined with the multiplication of gene copies method.

Alternatively, a promoter can be enhanced by, for example, introducing a mutation into the promoter to increase a transcription level of a gene located downstream of the promoter. Furthermore, it is known that substitution of several nucleotides in a spacer between the ribosome binding site (RBS) and start codon, and particularly, the sequences immediately upstream of the start codon profoundly affect the mRNA translatability. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984).

Methods for preparation of chromosomal DNA, hybridization, PCR, preparation of plasmid DNA, digestion and ligation of DNA, transformation, selection of an oligonucleotide as a primer and the like can be ordinary methods well known to one skilled in the art. These methods are described in Sambrook, J., and Russell D., "Molecular Cloning A Laboratory Manual, Third Edition", Cold Spring Harbor Laboratory Press (2001), and the like.

The bacterium of the present invention can be obtained by introduction of the aforementioned DNAs into a bacterium inherently having an ability to produce an L-amino acid. Alternatively, the bacterium of present invention can be obtained by imparting an ability to produce an L-amino acid to the bacterium already harboring the DNAs.

Examples of L-amino acid producing bacteria belonging to the genus *Escherichia* are described below.

L-Histidine Producing Bacteria

Examples of bacteria belonging to the genus *Escherichia* having L-histidine producing ability include L-histidine producing bacterium strains belonging to the genus *Escherichia*, such as *E. coli* strain 24 (VKPM B-5945, RU2003677); *E. coli* strain 80 (VKPM B-7270, RU2119536); *E. coli* strains NRRL B-12116-B12121 (U.S. Pat. No. 4,388,405); *E. coli* strains H-9342 (FERM BP-6675) and H-9343 (FERM BP-6676) (U.S. Pat. No. 6,344,347); *E. coli* strain H-9341 (FERM BP-6674) (EP1085087); *E. coli* strain AI80/pFM201 (U.S. Pat. No. 6,258,554) and the like.

Preferably, the bacterium of the present invention is further modified to enhance expression of genes of the histidine operon, which preferably includes the hisG gene encoding ATP phosphoribosyl transferase of which feedback inhibition by L-histidine is desensitized (Russian patents 2003677 and 2119536), for L-histidine producing bacteria.

L-Threonine-Producing Bacteria

Examples of parent strains for deriving the L-threonine-producing bacteria of the present invention include, but are not limited to, L-threonine-producing bacteria belonging to the genus *Escherichia*, such as *E. coli* strain TDH-6/pVIC40 (VKPM B-3996) (U.S. Pat. No. 5,175,107, U.S. Pat. No. 5,705,371), *E. coli* strain NRRL-21593 (U.S. Pat. No. 5,939,307), *E. coli* strain FERM BP-3756 (U.S. Pat. No. 5,474,918), *E. coli* strains FERM BP-3519 and FERM BP-3520 (U.S. Pat. No. 5,376,538), *E. coli* strain MG442 (Gusyatiner et al., Genetika (in Russian), 14, 947-956 (1978)), *E. coli* strains VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Dorozhny proezd. 1, Moscow 117545, Russian Federation) under the accession number B-3996.

Preferably, the bacterium of the present invention is further modified to enhance expression of one or more of the following genes:

the mutant thrA gene which codes for aspartokinase homoserine dehydrogenase I resistant to feed back inhibition by threonine;
the thrB gene which codes for homoserine kinase;
the thrC gene which codes for threonine synthase;
the rhtA gene which codes for a putative transmembrane protein;
the asd gene which codes for aspartate-β-semialdehyde dehydrogenase; and
the aspC gene which codes for aspartate aminotransferase (aspartate transaminase);

The thrA gene which encodes aspartokinase homoserine dehydrogenase I of *Escherichia coli* has been elucidated (nucleotide numbers 337 to 2799 in the sequence of GenBank accession NC_000913.2, gi: 49175990). The thrA gene is located between thrL and thrB genes on the chromosome of *E. coli* K-12. The thrB gene which encodes homoserine kinase of *Escherichia coli* has been elucidated (nucleotide numbers 2801 to 3733 in the sequence of GenBank accession NC_000913.2, gi: 49175990). The thrB gene is located between thrA and thrC genes on the chromosome of *E. coli* K-12. The thrC gene which encodes threonine synthase of *Escherichia coli* has been elucidated (nucleotide numbers 3734 to 5020 in the sequence of GenBank accession NC_000913.2, gi: 49175990). The thrC gene is located between thrB gene and yaaX open reading frame on the chromosome of *E. coli* K-12. All three genes function as a single threonine operon.

A mutant thrA gene which codes for aspartokinase homoserine dehydrogenase I resistant to feedback inhibition by threonine, as well as the thrB and thrC genes, can be obtained as one operon from the well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon that encodes components of the glutamine transport system, and the rhtA gene is identical to ORF1 (ybiF gene, numbers 764 to 1651 in the GenBank accession number AAA218541, gi:440181), located between the pexB and ompX genes. The unit expressing a protein encoded by the ORF1 has been designated rhtA (rht: resistance to homoserine and threonine) gene. Also, it was found that the rhtA23 mutation is an A-for-G substitution at position-1 with respect to the ATG start codon (ABSTRACTS of 17th International Congress of Biochemistry and Molecular Biology in conjugation with 1997 Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide numbers 3572511 to 3571408 in the sequence of GenBank accession NC_000913.1, gi: 16131307), and can be obtained by PCR (polymerase chain reaction; refer to White, T. J. et al., Trends Genet., 5, 185 (1989)) utilizing primers based on the nucleotide sequence of the gene. The asd genes of other microorganisms can be obtained in a similar manner.

Also, the aspC gene of *E. coli* has already been elucidated (nucleotide numbers 983742 to 984932 in the sequence of GenBank accession NC_000913.1, gi:16128895), and can be obtained by PCR. The aspC genes from other microorganisms can be obtained in a similar manner.

L-Lysine Producing Bacteria

Examples of L-lysine producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in a medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain, and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

L-Glutamic Acid Producing Bacteria

Examples of parent strains for deriving the L-glutamic acid-producing bacteria of the present invention include, but are not limited to, L-glutamic acid-producing bacteria belonging to the genus *Escherichia*, such as *E. coli* strain VL334thrC$^+$ (EP 1172433). *E. coli* strain VL334 (VKPM B-1641) is an L-isoleucine and L-threonine auxotrophic strain having mutations in the thrC and ilvA genes (U.S. Pat. No. 4,278,765). A wild-type allele of the thrC gene was transferred by the method of general transduction using a bacteriophage P1 grown on wild-type *E. coli* strain K12 (VKPM B-7) cells. As a result, an L-isoleucine auxotrophic strain VL334thrC$^+$ (VKPM B-8961) was obtained. This strain is able to produce L-glutamic acid.

Examples of parent strains for deriving the L-glutamic acid-producing bacteria of the present invention include mutants which are deficient in α-ketoglutarate dehydrogenase activity or have a reduced α-ketoglutarate dehydrogenase activity. Bacteria belonging to the genus *Escherichia* deficient in α-ketoglutarate dehydrogenase activity or having reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacteria, include mutant strains belonging to the genus *Pantoea* which are deficient in α-ketoglutarate dehydrogenase activity or have decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 and received an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Tryptophan Producing Bacteria

Examples of parent strains for deriving the L-tryptophan-producing bacteria of the present invention include, but are not limited to, L-tryptophan-producing bacteria belonging to the genus *Escherichia*, such as *E. coli* JP4735/pMU3028 (DSM10122) and JP6015/pMU91 (DSM10123) deficient in tryptophanyl-tRNA synthetase encoded by a mutant trpS gene (U.S. Pat. No. 5,756,345); *E. coli* SV164 (pGH5) having serA allele free from feedback inhibition by serine (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used.

Previously, it was identified that the yddG gene encodes a membrane protein which is not involved in a biosynthetic pathway of any L-amino acid. Also, the yddG gene is known to impart to a microorganism resistance to L-phenylalanine and several amino acid analogues when the wild-type allele of the gene is amplified on a multi-copy vector in the microorganism. Besides, the yddG gene can enhance production of L-phenylalanine or L-tryptophan when additional copies are introduced into the cells of the respective producing strain (WO03044192). So it is desirable that the L-tryptophan-producing bacterium be further modified to have enhanced expression of the yddG open reading frame.

L-Arginine Producing Bacterium

Examples of parent strains for deriving the L-arginine-producing bacteria of the present invention include, but are not limited to, L-arginine producing bacteria, such as *E. coli* strain 237 (VKPM B-7925) (US Patent Application US2002058315) and its derivative strains harboring mutant N-acetylglutamate synthase (Russian Patent Application No. 2001112869), *E. coli* strain 382 (VKPM B-7926) (European patent application EP1170358), an arginine-producing strain into which argA gene encoding N-acetylglutamate synthetase is introduced (JP 57-5693A), and the like.

L-Phenylalanine Producing Bacteria

Examples of parent strains for deriving the L-phenylalanine-producing bacteria of the present invention include, but are not limited to, L-phenylalanine producing bacteria belonging to the genus *Escherichia*, such as *E. coli* AJ12739 (tyrA::Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named AJ 12604 (FERM BP-3579) may be used (EP 488424 B1). Furthermore, L-phenylalanine producing bacteria belonging to the genus *Escherichia* with enhanced activity of the protein encoded by the yedA gene or the yddG gene may also be used (US patent applications 2003/0148473 A1 and 2003/0157667 A1).

L-Cysteine-Producing Bacteria

Examples of parent strains for deriving the L-cysteine-producing bacteria of the present invention include, but are not limited to, L-cysteine producing bacteria belonging to the genus *Escherichia*, such as *E. coli* strain JM15 which is transformed with different cysE alleles coding for feedback-resistant serine acetyltransferases (U.S. Pat. No. 6,218,168, Russian patent application 2003121601); *E. coli* strain W3110 having over-expressed genes which encode proteins suitable for secreting substances toxic for cells (U.S. Pat. No. 5,972,663); *E. coli* strains having lowered cysteine desulfohydrase activity (JP 11-155571A); *E. coli* strain W3110 with increased activity of a positive transcriptional regulator for cysteine regulon coded by the cysB gene (WO0127307A1), and the like.

L-Leucine Producing Bacteria

Examples of parent strains for deriving the L-leucine-producing bacteria of the present invention include, but are not limited to, L-leucine-producing bacteria belonging to the genus *Escherichia*, such as *E. coli* strains resistant to leucine analogs including β-2-thienylalanine, 3-hydroxyleucine, 4-azaleucine, 5,5,5-trifluoroleucine (JP 62-34397B and JP 08-70879A); *E. coli* strains obtained by the gene engineering method described in WO96/06926; *E. coli* strain H-9068 (JP 08-70879A), and the like.

The bacterium of the present invention may be improved by enhancing the expression of one or more genes involved in L-leucine biosynthesis. Examples include genes of the leuABCD operon, which are preferably represented by a mutant leuA gene coding for isopropylmalate synthase freed from feedback inhibition by L-leucine (U.S. Pat. No. 6,403,342). In addition, the bacterium of the present invention may be improved by enhancing the expression of one or more genes coding for proteins which excrete L-amino acid from the bacterial cell. Examples of such genes include the b2682 and b2683 genes (ygaZH genes) (Russian patent application 2001117632).

L-Proline Producing Bacterium

Examples of parent strains for deriving the L-proline-producing bacteria of the present invention include, but are not limited to, L-proline-producing bacteria belonging to the genus *Escherichia*, such as *E. coli* strain 702ilvA (VKPM B-8012) which is deficient in the ilvA gene, and is able to produce L-proline (EP 1172433). The bacterium of the present invention may be improved by enhancing the expression of one or more genes involved in L-proline biosynthesis. Examples of such genes for L-proline producing bacteria include the proB gene coding for glutamate kinase of which feedback inhibition by L-proline is desensitized (DE Patent 3127361). In addition, the bacterium of the present invention may be improved by enhancing the expression of one or more genes coding for proteins excreting L-amino acid from a bacterial cell. Such genes are exemplified by the b2682 and b2683 genes (ygaZH genes) (EP1239041 A2).

Examples of bacteria belonging to the genus *Escherichia* which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

The above-mentioned L-amino acid producing strains may be further modified for enhancement of the pentose assimilation rate or for enhancement of the L-amino acid biosynthetic ability by the wide scope of methods well known to the person skilled in the art.

The utilization rate for pentose sugars can be further enhanced by amplification of the pentose assimilation genes, araFG and araBAD genes for arabinose, or by mutations in the glucose assimilation systems (PTS and non-PTS), such as ptsG mutations (Nichols N. N. et al, Appl. Microbiol. Biotechnol., 2001, Jul. 56:1-2, 120-5).

The process of the present invention includes a process for producing an L-amino acid comprising the steps of cultivating the L-amino acid producing bacterium in a culture medium, allowing the L-amino acid to accumulate in the culture medium, and collecting the L-amino acid from the culture medium, wherein the culture medium contains a mixture of glucose and pentose sugars. Also, the method of present invention includes a method for producing L-histidine comprising the steps of cultivating the L-histidine producing bacterium of the present invention in a culture medium, allowing L-histidine to accumulate in the culture medium, and collecting L-histidine from the culture medium, wherein the culture medium contains a mixture of glucose and pentose sugars. Also, the method of present invention includes a method for producing L-threonine comprising the steps of cultivating the L-threonine producing bacterium of the present invention in a culture medium, allowing L-threonine to accumulate in the culture medium, and collecting L-threonine from the culture medium, wherein the culture medium contains a mixture of glucose and pentose sugars. Also, the method of present invention includes a method for producing L-lysine comprising the steps of cultivating the L-lysine producing bacterium of the present invention in a culture medium, allowing L-lysine to accumulate in the culture medium, and collecting L-lysine from the culture medium, wherein the culture medium contains a mixture of glucose and pentose sugars. Also, the method of present invention includes a method for producing L-glutamic acid comprising the steps of cultivating the L-glutamic acid producing bacterium of the present invention in a culture medium, allowing L-glutamic acid to accumulate in the culture medium, and collecting L-glutamic acid from the culture medium, wherein the culture medium contains a mixture of glucose and pentose sugars. Also, the method of present invention includes a method for producing L-tryptophan comprising the steps of cultivating the L-tryptophan producing bacterium of the present invention in a culture medium, allowing L-tryptophan to accumulate in the culture medium, and collecting L-tryptophan from the culture medium, wherein the culture medium contains a mixture of glucose and pentose sugars.

The mixture of pentose sugars, such as xylose and arabinose, along with hexose sugar, such as glucose, can be obtained from under-utilized sources of biomass. Glucose, xylose, arabinose and other carbohydrates are liberated from plant biomass by steam and/or concentrated acid hydrolysis, dilute acid hydrolysis, hydrolysis using enzymes, such as cellulase, or alkali treatment. When the substrate is cellulosic material, the cellulose may be hydrolyzed to sugars simultaneously or separately and also fermented to L-amino acid. Since hemicellulose is generally easier to hydrolyze to sugars than cellulose, it is preferable to prehydrolyze the cellulosic material, separate the pentoses and then hydrolyze the cellulose by treatment with steam, acid, alkali, cellulases or combinations thereof to form glucose.

A mixture consisting of different ratios of glucose/xylose/arabinose was used in this study to approximate the composition of feed stock mixture of glucose and pentoses, which could potentially be derived from plant hydrolysates (see Example section).

In the present invention, the cultivation, collection, and purification of L-amino acids from the medium and the like may be performed in a manner similar to a conventional fermentation method wherein an amino acid is produced using a microorganism. The medium used for culture may be either a synthetic medium or a natural medium, so long as the medium includes a carbon source and a nitrogen source and minerals and, if necessary, appropriate amounts of nutrients which the microorganism requires for growth.

The carbon source may include various carbohydrates such as glucose, sucrose, arabinose, xylose and other pentose and hexose sugars, which the L-amino acid producing bacterium could utilize as a carbon source. Glucose, xylose, arabinose and other carbohydrates may be a part of feed stock mixture of sugars obtained from cellulosic biomass.

Pentose sugars suitable for fermentation in the present invention include, but are not limited to xylose and arabinose.

As the nitrogen source, various ammonium salts such as ammonia and ammonium sulfate, other nitrogen compounds such as amines, a natural nitrogen source such as peptone, soybean-hydrolysate and digested fermentative microorganism are used. As minerals, potassium monophosphate, magnesium sulfate, sodium chloride, ferrous sulfate, manganese sulfate, calcium chloride, and the like are used. Additional nutrients can be added to the medium if necessary. For instance, if the microorganism requires proline for growth (proline auxotrophy) a sufficient amount of proline can be added to the medium for cultivation.

Preferably, the cultivation is performed under aerobic conditions such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by ion-exchange, concentration and crystallization methods.

EXAMPLES

The present invention will be more concretely explained below with reference to the following non-limiting examples.

Example 1

Cloning the xylABFGHR Locus from the Chromosome of *E. coli* Strain MG1655

Based on genome analysis of *E. coli* strain MG1655, the genes xylABFGHR can be cloned as a single HindIII fragment (13.1 kb) of 556 HindIII chromosomal fragments in total (FIG. 1). For that purpose, a gene library was constructed using vector pUC19, which is capable of surviving in *E. coli* with insertions of that size.

To construct such a library, chromosomal DNA of MG1655 was digested with HindIII restrictases and the pUC19 vector was digested with XbaI restrictase. The strain MG1655 (ATCC47076, ATCC700926) can be obtained from American Type Culture Collection (10801 University Boulevard, Manassas, Va., 20110-2209, U.S.A.).

Sticky ends in both DNA preparations were subsequently filled by Kienow fragment so as to prevent self-ligation (two bases filling). After the ligation procedure a pool of recombinant pUC19 plasmids was obtained. The size of the library is more then 200 thousand clones. The gene library was analyzed by PCR using primers complementary to the plasmid sequence and primers complementary to the cloning chromosomal fragment. DNA fragments with appropriate molecular weights were not found among the PCR products, which was interpreted to mean that the fragment corresponding to the xylABFGHR operon was missing from the constructed library. This result may be due to the negative influence of the malS gene, and the yiaA and yiaB ORFs (with unknown function), which are also present in the HindIII fragment of interest. Another possible reason for negative selection is the large size of the Xyl-locus. To overcome this problem, new gene libraries were constructed based on a modified pUC19 plasmid. The main approach is to clone Xyl-locus as a set of fragments without of the adjacent malS gene and yiaA and yiaB ORFs.

For that purpose, a polylinker of plasmid pUC19 was modified by inserting a synthetic DNA fragment containing MluI restriction site. Two gene libraries were constructed in the modified pUC19 cloning vector. The first library was created by digestion of the chromosomal DNA of strain MG1655 and the modified pUC19 with HindIII and MluI restrictases followed by ligation. The library volume was more than 4,000 clones. The gene library was analyzed by PCR using primers complementary to the plasmid sequence, and primers 1 (SEQ ID NO:13) and 2 (SEQ ID NO:14) which are complementary to the fragment xylABFG of the xyl locus. The expected DNA fragments with appropriate molecular weights were found among the PCR products. The next step was to saturate the gene library with a fragment of interest. To this end, DNA from the original gene library was digested by endonucleases, restriction sites of which do not exist in the fragment of interest. There are Eco147I, KpnI, MlsI, Bst1107I. The frequency of the plasmid of interest in the enriched library was ⅛₀₀ clones. The enriched library was analyzed by PCR as described above. After five sequential enrichments of the library the cell population, only ten clones containing xylABFG genes were found. The resulting plasmid containing HindIII-MluI DNA fragment with genes xylABFG was designated as pUC19/xylA-G. Then the HindIII-Mph1103I fragment containing the yiaA and yiaB ORFs was eliminated from plasmid pUC19/xylA-G; sticky ends were blunted by Klenow fragment and a synthetic linker containing an EcoRI restriction site was inserted by ligation. Thus, the plasmid pUC19/xylA-G-2 was obtained. Then, the resulting pUC19/xylA-G-2 plasmid was cut by an EheI restrictase; sticky ends were blunted by Klenow fragment and synthetic linker containing HindIII restriction site was inserted by ligation. Thus the pUC19/xylA-G-3 plasmid was obtained. A HindIII restriction site was inserted with the remaining DNA fragment containing xylHR genes, resulting in the complete xyl locus.

The second library was created by digestion of the chromosomal DNA from strain MG1655 and a modified pUC19 with PstI and MluI restrictases, followed by ligation. The library volume was more than 6,000 clones. The gene library was analyzed by PCR using primers complementary to the plasmid sequence and primers 3 (SEQ ID NO:15) and 4 (SEQ ID NO:16), which are complementary to the cloning chromosomal fragment. DNA fragments with appropriate molecular weights were found among the PCR products. The next step was a sequential subdivision of the gene library on cell population with known size, accompanied by PCR analysis. After seven sequential subdivision of library the cell population containing genes xylHR contained only ten clones. Among this population, a fragment DNA of interest was found by restriction analysis. The resulting plasmid containing PstI-MluI DNA fragment with xy/HR genes was designated as pUC19/xylHR. Then, HindIII-MluI DNA fragment from plasmid pUC19/xylHR was ligated to the pUC19/xylA-G-3 plasmid, which had been previously treated with HindIII and MluI restrictases. Finally, the complete xyl locus of strain MG1655 was obtained. The resulting multicopy plasmid containing the complete xylABFGHR locus was designated pUC19/xylA-R.

Then HindIII-EcoRI DNA fragment from the pUC19/xylA-R plasmid was recloned into the low copy vector pMW119mod, which had been previously digested with HindIII and EcoRI restrictases, resulting in the low copy plasmid pMW119mod-xylA-R which contained the complete xylABFGHR locus. The low copy vector pMW119mod was obtained from the commercially available pMW119 vector by elimination of the PvuII-PvuII fragment. This fragment contains the multi-cloning site and was a major part of the lacZ gene. The lacZ gene contains sites for lacI repressor followed by insertion of synthetic linker containing EcoRI and HindIII sites, which are necessary for insertion of the xylABFGHR locus from the pUC19/xylA-R plasmid.

Example 2

Production of L-Histidine by L-Histidine Producing Bacterium from Fermentation of a Mixture of Glucose and Pentoses L-histidine producing E. Coli strain 80 was used as a strain for production of L-histidine by fermentation of a mixture of glucose and pentoses. E. Coli strain 80 (VKPM B-7270) is described in detail in Russian patent RU2119536 and has been deposited in the Russian National Collection of Industrial Microorganisms (Russia, 113545 Moscow, 1st Dorozhny proezd, 1) on Oct. 15, 1999 under accession number VRPM B-7270. Then, it was transferred to an international deposit under the provisions of the Budapest Treaty on Jul. 12, 2004. Transformation of strain 80 with the pMW119mod-xylA-R plasmid was performed by ordinary methods, yielding strain 80/pMW119mod-xylA-R.

To obtain the seed culture, both strains 80 and 80/pMW119mod-xylA-R were grown on a rotary shaker (250 rpm) at 27° C. for 6 hours in 40 ml test tubes (Ø18 mm) containing 2 ml of L-broth with 1 g/l of streptomycin. For the strain 80/pMW119mod-xylA-R, 100 mg/l ampicillin was additionally added. Then, 2 ml (5%) of seed material was inoculated into the fermentation medium. Fermentation was carried out on a rotary shaker (250 rpm) at 27° C. for 65 hours in 40 ml test tubes containing 2 ml of fermentation medium.

After cultivation, the amount of L-histidine which had accumulated in the culture medium was determined by paper chromatography. The composition of the mobile phase is the following: butanol:acetate:water=4:1:1 (v/v). A solution (0.5%) of ninhydrin in acetone was used as a visualizing reagent. The results are presented in Table 2.

The composition of the fermentation medium (g/l):

| | |
|---|---|
| Carbohydrates (total) | 100.0 |
| Mameno (soybean hydrolysate) | 0.2 of TN (total nitrogen) |
| L-proline | 0.8 |
| $(NH_4)_2SO_4$ | 25.0 |
| $K_2HPO_4$ | 2.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.001 |
| Betaine | 2.0 |
| $CaCO_3$ | 6.0 |
| Streptomycin | 1.0 |

Carbohydrates (glucose, arabinose, xylose), L-proline, betaine and magnesium sulfate are sterilized separately. $CaCO_3$ dry-heat are sterilized at 110° C. for 30 min. pH is adjusted to 6.0 by KOH before sterilization. As can be seen from Table 2, increased expression of the xylABFGHR locus improved productivity of the L-histidine producing E. coli strain 80 which had been cultured in the medium containing xylose.

TABLE 2

| | Glucose | | Xylose | | Glucose/xylose 1:1 | | Arabinose | | Glucose/arabinose 1:1 | |
|---|---|---|---|---|---|---|---|---|---|---|
| Strain | $OD_{450}$ | His, g/l | $OD_{450}$ | His, g/l | $OD_{450}$ | His, g/l | $OD_{450}$ | His, g/l | $OD_{450}$ | His, g/l |
| 80 | 43 | 8.9 | No growth | 0.4 | 39 | 3.2 | 37 | 10.3 | 40 | 8.7 |
| 80/pMW119mod-xylA-R | 39 | 9.3 | 50 | 9.6 | 39 | 9.9 | 36 | 10.5 | 40 | 9.1. |

Example 3

Production of L-Threonine by Fermentation of a Mixture of Glucose and Pentoses Using L-Threonine Producing Bacterium L-threonine producing *E. coli* strain B-3996 was used to evaluate production of L-threonine by fermentation of a mixture of glucose and pentose. Transformation of strain B-3996 with the pMW119mod-xylA-R plasmid and vector pMW119 was performed by an ordinary method using $CaCl_2$, yielding strains 3996/pMW119mod-xylA-R and 3996/pMW119, respectively.

Both *E. coli* strains B-3996/pMW119 and B-3996/pMW119mod-xylA-R were grown for 12-15 hours at 37° C. on L-agar plates containing streptomycin (50 mg/l) and ampicillin (150 mg/l). Then, the fermentation medium containing the carbon source xylose (4%) was inoculated with one loop of the strains. The fermentation was performed in 2 ml of fermentatin medium containing streptomycin (50 mg/l) in 20×200 mm test tubes. Cells were grown for 25 hours at 32° C. with shaking at 250 rpm.

After cultivation, the amount of L-threonine which has accumulated in the medium was determined by paper chromatography using the following mobile phase: butanol:acetic acid:water=4:1:1 (v/v). A solution (2%) of ninhydrin in acetone was used as a visualizing reagent. A spot containing L-threonine was cut out, L-threonine was eluted in 0.5% water solution of $CdCl_2$, and the amount of L-threonine was estimated spectrophotometrically at 540 nm. The results are presented in Table 3.

The composition of the fermentation medium (g/l) is as follows:

| | |
|---|---|
| Carbohydrates | 40.0 |
| $(NH_4)_2SO_4$ | 24.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 |

Glucose and magnesium sulfate are sterilized separately. $CaCO_3$ dry-heat is sterilized at 180° C. for 2 h. The pH is adjusted to 7.0. Antibiotic is introduced into the medium after sterilization.

TABLE 3

| | Xylose | |
|---|---|---|
| Strain | $OD_{540}$ | Thr, g/l |
| B-3996/pMW119 | 13.9 ± 1.0 | 7.0 ± 0.2 |
| B-3996/pMW119mod-xylA-R | 16.1 ± 0.9 | 9.3 ± 0.9 |

As can be seen from Table 3, increased expression of the xylABFGHR locus improved productivity of the L-threonine producing *E. coli* strain B-3996/pMW119 which had been cultured in the medium containing xylose.

Example 4

Production of L-Lysine by Fermentation of a Mixture of Glucose and Pentoses Using L-Lysine Producing Bacterium L-lysine producing *E. coli* strain WC196ΔcadA Δldc was used to evaluate production of L-lysine by fermentation of a mixture of glucose and pentose. Strain WC196ΔcadA ΔldcC was obtained from strain WC196 by inactivation of lysine decarboxylases coded by ldcC gene and cadA gene as it was described in U.S. Pat. No. 5,827,698. Transformation of strain WC196ΔcadA Δldc with the pMW119mod-xylA-R plasmid and vector pMW119 was performed by an ordinary method using $CaCl_2$, yielding strains WC196ΔcadA ΔldcpMW119mod-xylA-R and WC196ΔcadA Δldc/pMW119, respectively.

Both *E. coli* strains WC196ΔcadA Δldc/pMW119 and WC196ΔcadA Δldc/pMW119mod-xylA-R were grown for 12-15 hours at 37° C. on L-agar plates containing ampicillin (150 mg/l). Then, the fermentation medium containing either xylose (4%) or a xylose (2%)/glucose (2%) mixture as a carbon source was inoculated with one loop of strains. The fermentation was performed in 2 ml of fermentation medium 20×200 mm test tubes. Cells were grown for 25 hours at 32° C. with shaking at 250 rpm.

After cultivation, the amount of L-lysine which has accumulated in the medium was determined by paper chromatography using the following mobile phase: butanol:acetic acid:water=4:1:1 (v/v). A solution (2%) of ninhydrin in acetone was used as a visualizing reagent. A spot containing L-lysine was cut out, L-lysine was eluted in 0.5% water solution of $CdCl_2$, and the amount of L-lysine was estimated spectrophotometrically at 540 nm. The results are presented in Table 4.

The composition of the fermentation medium (g/l) is as follows:

| | |
|---|---|
| Carbohydrates | 40.0 |
| $(NH_4)_2SO_4$ | 24.0 |
| $KH_2PO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |
| $CaCO_3$ | 30.0 |

Glucose and magnesium sulfate are sterilized separately. $CaCO_3$ dry-heat is sterilized at 180° C. for 2 h. The pH is adjusted to 7.0 with KOH. Antibiotic is introduced into the medium after sterilization.

TABLE 4

| | Xylose | | Glucose/xylose 1:1 | |
|---|---|---|---|---|
| Strain | $OD_{540}$ | Lys, g/l | $OD_{540}$ | Lys, g/l |
| WC196ΔcadA Δldc/pMW119 | 5.7 ± 0.2 | 0.0 | 24.5 ± 0.2 | 1.0 ± 0.3 |
| WC196ΔcadA Δldc/pMW119mod-xylA-R | 35.2 ± 0.7 | 1.8 ± 0.2 | 36.7 ± 0.2 | 2.0 ± 0.3 |

As can be seen from Table 4, increased expression of the xylABFGHR locus improved productivity of the L-lysine producing *E. coli* strain WC196ΔcadA Δldc/pMW119 cultured in the medium containing xylose.

Example 5

Production of L-Glutamic Acid by Fermentation of a Mixture of Glucose and Pentoses Using L-Glutamic Acid Producing Bacterium L-glutamic acid producing *E. coli* strain AJ12624 was used to evaluate production of L-glutamic acid by fermentation of a mixture of glucose and pentose. Transformation of strain AJ12624 with the pMW119mod-xylA-R plasmid and vector pMW119 was performed by ordinary method using $CaCl_2$, yielding strains AJ12624/pMW119mod-xylA-R and AJ12624/pMW119, respectively.

Both *E. coli* strains AJ12624/pMW119 and AJ12624/pMW119mod-xylA-R were grown for 12-15 hours at 37° C. on L-agar plates containing ampicillin (150 mg/l). Then, the fermentation medium containing xylose (4%) as a carbon source was inoculated with one loop of strains. The fermentation was performed in 2 ml of fermentatin medium in 20×200 mm test tubes. Cells were grown for 48 hours at 32° C. with shaking at 250 rpm.

After cultivation, the amount of L-glutamic acid which has accumulated in the medium was determined by paper chromatography using the following mobile phase: butanol:acetic acid:water=4:1:1 (v/v). A solution (2%) of ninhydrin in acetone was used as a visualizing reagent. A spot containing L-glutamic acid was cut out, L-glutamic acid was eluted in 0.5% water solution of $CdCl_2$, and the amount of L-glutamic acid was estimated spectrophotometrically at 540 nm. The results are presented in Table 5.

The composition of the fermentation medium (g/l):

| | |
|---|---|
| Carbohydrates | 40.0 |
| $(NH_4)_2SO_4$ | 25.0 |
| $KH_2PO_4$ | 2.0 |
| $MgSO_4 \cdot 7H_2O$ | 1.0 |
| Thiamine HCl | 0.0001 |
| L-isoleucine | 0.07 |
| $CaCO_3$ | 25.0 |

Glucose and magnesium sulfate are sterilized separately. $CaCO_3$ dry-heat sterilized at 180° C. for 2 h. pH is adjusted to 7.2.

TABLE 5

| | Xylose | |
|---|---|---|
| Strain | $OD_{540}$ | Glu, g/l |
| AJ12624/pMW119 | 8.6 ± 0.3 | 4.5 ± 0.2 |
| AJ12624/pMW119mod-xylA-R | 8.0 ± 0.2 | 5.3 ± 0.2 |

As can be seen from Table 5, increased expression of the xylABFGHR locus improved productivity of the L-glutamic acid producing *E. Coli* strain AJ12624/pMW119 which had been cultured in the medium containing xylose.

Example 6

Production of L-Tryptophan by Fermentation of a Mixture of Glucose and Pentoses Using L-Tryptophan Producing Bacterium L-tryptophan producing *E. Coli* strain SV164/pGH5 was used to evaluate production of L-tryptophan by fermentation of a mixture of glucose and pentose. Transformation of strain SV164/pGH5 with the pMW119mod-xylA-R plasmid and vector pMW119 was performed by ordinary method using $CaCl_2$, yielding strains SV164/pGH5/pMW119mod-xylA-R and SV164/pGH5/pMW119, respectively.

Both *E. coli* strains SV164/pGH5/pMW119 and SV164/pGH5/pMW119mod-xylA-R were grown for 12-15 hours at 37° C. on L-agar plates containing tetracycline (30 mg/l) and ampicillin (150 mg/l). Then, the fermentation medium containing either xylose (4%) or xylose (2%)/glucose (2%) mixture as a carbon source was inoculated with one loop of strains. The fermentation was performed in 2 ml of fermentatin medium in 20×200 mm test tubes. Cells were grown for 48 hours at 30° C. with shaking at 250 rpm.

After cultivation, the amount of L-tryptophan which has accumulated in the medium was determined by TLC. 10×15 cm TLC plates coated with 0.11 mm layers of Sorbfil silica gel without fluorescent indicator (Stock Company Sorbpolymer, Krasnodar, Russia) can be used. Sorbfil plates can be developed with a mobile phase: propan-2-ol:ethylacetate:25% aqueous ammonia: water=40:40:7:16 (v/v). A solution (2%) of ninhydrin in acetone can be used as a visualizing reagent. The results are presented in Table 7. The fermentation medium components are set forth in Table 5, but should be sterilized in separate groups A, B, C, D, E, F, and H, as shown, to avoid adverse interactions during sterilization.

TABLE 6

| Solutions | Component | Final concentration, g/l |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno (total N) | 0.07 |
| B | Glucose | 40.0 |
| | $MgSO_4 \cdot 7H_2O$ | 0.3 |
| C | $CaCl_2$ | 0.011 |
| D | $FeSO_4 \cdot 7H_2O$ | 0.075 |
| | Sodium citrate | 1.0 |
| E | $Na_2MoO_4 \cdot 2H_2O$ | 0.00015 |
| | $H_3BO_3$ | 0.0025 |
| | $CoCl_2 \cdot 6H_2O$ | 0.00007 |
| | $CuSO_4 \cdot 5H_2O$ | 0.00025 |
| | $MnCl_2 \cdot 4H_2O$ | 0.0016 |
| | $ZnSO_4 \cdot 7H_2O$ | 0.0003 |
| F | Thiamine HCl | 0.005 |
| G | $CaCO_3$ | 30.0 |
| H | Pyridoxine | 0.03 |

Solution A had pH 7.1 adjusted by $NH_4OH$.

TABLE 7

| | Xylose | | Glucose/xylose 1:1 | |
|---|---|---|---|---|
| Strain | $OD_{540}$ | Trp, g/l | $OD_{540}$ | Trp, g/l |
| SV164/pGH5/pMW119 | 3.5 ± 0.4 | 0.5 ± 0.2 | 15.3 ± 0.2 | 5.3 ± 0.7 |
| SV164/pGH5/pMW119mod-xylA-R | 13.9 ± 0.5 | 3.6 ± 0.5 | 15.1 ± 0.8 | 6.0 ± 0.5 |

As can be seen from Table 7, increased expression of the xylABFGHR locus improved productivity of the L-tryptophan producing *E. Coli* strain SV164/pGH5/pMW119 cultured in the medium containing xylose.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety, including the foreign priority documents RU2004107548, filed Mar. 16, 2004 and RU2005106720, filed Mar. 14, 2005.

What is claimed is:

1. A method for producing an L-amino acid, comprising
A) cultivating an L-amino acid-producing *Escherichia coli* (*E. coli*) in a culture medium containing a mixture of glucose and pentose sugars, and
B) collecting the L-amino acid from the culture medium, wherein said *E. coli* has been modified to have enhanced activities of xylose utilization enzymes as compared to a non-modified *E. coli*,
wherein said activities are enhanced by increasing the expression of the xylABFGHR locus using a method selected from the group consisting of:
A) increasing the copy number of the xylABFGHR locus,
B) placing the locus under the control of a promoter which is more potent than the native promoter, and
C) combinations thereof.

2. The method according to claim 1, wherein the copy number is increased by transforming the *E. coli* with a multi-copy vector harboring the xylABFGHR locus.

3. The method according to claim 1, wherein said xylABFGHR locus originates from a bacterium belonging to the genus *Escherichia*.

4. The method according to claim 1, wherein said pentose sugars are arabinose and xylose.

5. The method according to claim 1, wherein the mixture is a feedstock mixture of sugars obtained from cellulosic biomass.

6. The method according to claim 1, wherein the L-amino acid is L-threonine.

7. The method according to claim 6, wherein the bacterium has enhanced expression of genes for L-threonine biosynthesis.

8. The method according to claim 1, wherein said xylABFGHR locus originates from *E. coli*.

9. The method according to claim 1, wherein said xylABFGHR locus comprises an xylA gene which encodes the amino acid sequence shown in SEQ ID NO: 2, an xylB gene which encodes the amino acid sequence shown in SEQ ID NO:4, an xylF gene which encodes the amino acid sequence shown in SEQ ID NO: 6, an xylG gene which encodes the amino acid sequence shown in SEQ ID NO: 8, an xylH gene which encodes the amino acid sequence shown in SEQ ID NO: 10, and an xylR gene which encodes the amino acid sequence shown in SEQ ID NO: 12.

10. The method according to claim 1, wherein the L-amino acid is L-histidine.

11. The method according to claim 10, wherein the bacterium has enhanced expression of genes for L-histidine biosynthesis.

12. The method according to claim 1, wherein the L-amino acid is L-lysine.

13. The method according to claim 12, wherein the bacterium has enhanced expression of genes for L-lysine biosynthesis.

14. The method according to claim 1, wherein the L-amino acid is L-glutamic acid.

15. The method according to claim 14, wherein the bacterium has enhanced expression of genes for L-glutamic acid biosynthesis.

16. The method according to claim 1, wherein the L-amino acid is L-tryptophan.

17. The method according to claim 16, wherein the bacterium has enhanced expression of genes for L-tryptophan biosynthesis.

* * * * *

SEQUENCE LISTING

<160> NUMBER OF SEQ ID NOS: 16

<210> SEQ ID NO 1
<211> LENGTH: 1323
<212> TYPE: DNA
<213> ORGANISM: Escherichia coli
<220> FEATURE:
<221> NAME/KEY: CDS
<222> LOCATION: (1)..(1323)

<400> SEQUENCE: 1

| | | | | | | | | | | | | | | | | |
|---|---|---|---|---|---|---|---|---|---|---|---|---|---|---|---|---|
| atg | caa | gcc | tat | ttt | gac | cag | ctc | gat | cgc | gtt | cgt | tat | gaa | ggc | tca | 48 |
| Met | Gln | Ala | Tyr | Phe | Asp | Gln | Leu | Asp | Arg | Val | Arg | Tyr | Glu | Gly | Ser | |
| 1 | | | | 5 | | | | | 10 | | | | | 15 | | |
| aaa | tcc | tca | aac | ccg | tta | gca | ttc | cgt | cac | tac | aat | ccc | gac | gaa | ctg | 96 |
| Lys | Ser | Ser | Asn | Pro | Leu | Ala | Phe | Arg | His | Tyr | Asn | Pro | Asp | Glu | Leu | |
| | | | 20 | | | | | 25 | | | | | 30 | | | |
| gtg | ttg | ggt | aag | cgt | atg | gaa | gag | cac | ttg | cgt | ttt | gcc | gcc | tgc | tac | 144 |
| Val | Leu | Gly | Lys | Arg | Met | Glu | Glu | His | Leu | Arg | Phe | Ala | Ala | Cys | Tyr | |
| | | 35 | | | | | 40 | | | | | 45 | | | | |
| tgg | cac | acc | ttc | tgc | tgg | aac | ggg | gcg | gat | atg | ttt | ggt | gtg | ggg | gcg | 192 |
| Trp | His | Thr | Phe | Cys | Trp | Asn | Gly | Ala | Asp | Met | Phe | Gly | Val | Gly | Ala | |
| | 50 | | | | | 55 | | | | | 60 | | | | | |
| ttt | aat | cgt | ccg | tgg | cag | cag | cct | ggt | gag | gca | ctg | gcg | ttg | gcg | aag | 240 |
| Phe | Asn | Arg | Pro | Trp | Gln | Gln | Pro | Gly | Glu | Ala | Leu | Ala | Leu | Ala | Lys | |
| 65 | | | | | 70 | | | | | 75 | | | | | 80 | |
| cgt | aaa | gca | gat | gtc | gca | ttt | gag | ttt | ttc | cac | aag | tta | cat | gtg | cca | 288 |
| Arg | Lys | Ala | Asp | Val | Ala | Phe | Glu | Phe | Phe | His | Lys | Leu | His | Val | Pro | |
| | | | | 85 | | | | | 90 | | | | | 95 | | |
| ttt | tat | tgc | ttc | cac | gat | gtg | gat | gtt | tcc | cct | gag | ggc | gcg | tcg | tta | 336 |
| Phe | Tyr | Cys | Phe | His | Asp | Val | Asp | Val | Ser | Pro | Glu | Gly | Ala | Ser | Leu | |
| | | | 100 | | | | | 105 | | | | | 110 | | | |
| aaa | gag | tac | atc | aat | aat | ttt | gcg | caa | atg | gtt | gat | gtc | ctg | gca | ggc | 384 |
| Lys | Glu | Tyr | Ile | Asn | Asn | Phe | Ala | Gln | Met | Val | Asp | Val | Leu | Ala | Gly | |
| | | 115 | | | | | 120 | | | | | 125 | | | | |
| aag | caa | gaa | gag | agc | ggc | gtg | aag | ctg | ctg | tgg | gga | acg | gcc | aac | tgc | 432 |
| Lys | Gln | Glu | Glu | Ser | Gly | Val | Lys | Leu | Leu | Trp | Gly | Thr | Ala | Asn | Cys | |
| | 130 | | | | | 135 | | | | | 140 | | | | | |
| ttt | aca | aac | cct | cgc | tac | ggc | gcg | ggt | gcg | gcg | acg | aac | cca | gat | cct | 480 |
| Phe | Thr | Asn | Pro | Arg | Tyr | Gly | Ala | Gly | Ala | Ala | Thr | Asn | Pro | Asp | Pro | |
| 145 | | | | | 150 | | | | | 155 | | | | | 160 | |
| gaa | gtc | ttc | agc | tgg | gcg | gca | acg | caa | gtt | gtt | aca | gcg | atg | gaa | gca | 528 |
| Glu | Val | Phe | Ser | Trp | Ala | Ala | Thr | Gln | Val | Val | Thr | Ala | Met | Glu | Ala | |
| | | | | 165 | | | | | 170 | | | | | 175 | | |
| acc | cat | aaa | ttg | ggc | ggt | gaa | aac | tat | gtc | ctg | tgg | ggc | ggt | cgt | gaa | 576 |
| Thr | His | Lys | Leu | Gly | Gly | Glu | Asn | Tyr | Val | Leu | Trp | Gly | Gly | Arg | Glu | |
| | | | 180 | | | | | 185 | | | | | 190 | | | |
| ggt | tac | gaa | acg | ctg | tta | aat | acc | gac | ttg | cgt | cag | gag | cgt | gaa | caa | 624 |
| Gly | Tyr | Glu | Thr | Leu | Leu | Asn | Thr | Asp | Leu | Arg | Gln | Glu | Arg | Glu | Gln | |
| | | 195 | | | | | 200 | | | | | 205 | | | | |
| ctg | ggc | cgc | ttt | atg | cag | atg | gtg | gtt | gag | cat | aaa | cat | aaa | atc | ggt | 672 |
| Leu | Gly | Arg | Phe | Met | Gln | Met | Val | Val | Glu | His | Lys | His | Lys | Ile | Gly | |
| | 210 | | | | | 215 | | | | | 220 | | | | | |
| ttc | cag | ggc | acg | ttg | ctt | atc | gaa | ccg | aaa | ccg | caa | gaa | ccg | acc | aaa | 720 |
| Phe | Gln | Gly | Thr | Leu | Leu | Ile | Glu | Pro | Lys | Pro | Gln | Glu | Pro | Thr | Lys | |
| 225 | | | | | 230 | | | | | 235 | | | | | 240 | |
| cat | caa | tat | gat | tac | gat | gcc | gcg | acg | gtc | tat | ggc | ttc | ctg | aaa | cag | 768 |
| His | Gln | Tyr | Asp | Tyr | Asp | Ala | Ala | Thr | Val | Tyr | Gly | Phe | Leu | Lys | Gln | |
| | | | | 245 | | | | | 250 | | | | | 255 | | |
| ttt | ggt | ctg | gaa | aaa | gag | att | aaa | ctg | aac | att | gaa | gct | aac | cac | gcg | 816 |

```
Phe Gly Leu Glu Lys Glu Ile Lys Leu Asn Ile Glu Ala Asn His Ala
            260             265                 270 acg ctg gca ggt cac tct ttc cat cat gaa ata gcc acc gcc att gcg      864
Thr Leu Ala Gly His Ser Phe His His Glu Ile Ala Thr Ala Ile Ala
        275                 280                 285 ctt ggc ctg ttc ggt tct gtc gac gcc aac cgt ggc gat gcg caa ctg      912
Leu Gly Leu Phe Gly Ser Val Asp Ala Asn Arg Gly Asp Ala Gln Leu
        290                 295                 300 ggc tgg gac acc gac cag ttc ccg aac agt gtg gaa gag aat gcg ctg      960
Gly Trp Asp Thr Asp Gln Phe Pro Asn Ser Val Glu Glu Asn Ala Leu
305                 310                 315                 320 gtg atg tat gaa att ctc aaa gca ggc ggt ttc acc acc ggt ggt ctg     1008
Val Met Tyr Glu Ile Leu Lys Ala Gly Gly Phe Thr Thr Gly Gly Leu
                325                 330                 335 aac ttc gat gcc aaa gta cgt cgt caa agt act gat aaa tat gat ctg     1056
Asn Phe Asp Ala Lys Val Arg Arg Gln Ser Thr Asp Lys Tyr Asp Leu
            340                 345                 350 ttt tac ggt cat atc ggc gcg atg gat acg atg gca ctg gcg ctg aaa     1104
Phe Tyr Gly His Ile Gly Ala Met Asp Thr Met Ala Leu Ala Leu Lys
        355                 360                 365 att gca gcg cgc atg att gaa gat ggc gag ctg gat aaa cgc atc gcg     1152
Ile Ala Ala Arg Met Ile Glu Asp Gly Glu Leu Asp Lys Arg Ile Ala
370                 375                 380 cag cgt tat tcc ggc tgg aat agc gaa ttg ggc cag caa atc ctg aaa     1200
Gln Arg Tyr Ser Gly Trp Asn Ser Glu Leu Gly Gln Gln Ile Leu Lys
385                 390                 395                 400 ggc caa atg tca ctg gca gat tta gcc aaa tat gct cag gaa cat cat     1248
Gly Gln Met Ser Leu Ala Asp Leu Ala Lys Tyr Ala Gln Glu His His
                405                 410                 415 ttg tct ccg gtg cat cag agt ggt cgc cag gaa caa ctg gaa aat ctg     1296
Leu Ser Pro Val His Gln Ser Gly Arg Gln Glu Gln Leu Glu Asn Leu
            420                 425                 430 gta aac cat tat ctg ttc gac aaa taa                                 1323
Val Asn His Tyr Leu Phe Asp Lys
        435                 440

<210> SEQ ID NO 2
<211> LENGTH: 440
<212> TYPE: PRT
<213> ORGANISM: Escherichia coli

<400> SEQUENCE: 2

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
```

```
                    130                 135                 140
Phe Thr Asn Pro Arg Tyr Gly Ala Gly Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
                180                 185                 190

Gly Tyr Glu Thr Leu Leu Asn Thr Asp Leu Arg Gln Glu Arg Glu Gln
                195                 200                 205

Leu Gly Arg Phe Met Gln Met Val Val Glu His Lys His Lys Ile Gly
210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
                260                 265                 270

Thr Leu Ala Gly His Ser Phe His His Glu Ile Ala Thr Ala Ile Ala
                275                 280                 285

Leu Gly Leu Phe Gly Ser Val Asp Ala Asn Arg Gly Asp Ala Gln Leu
                290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
                340                 345                 350

Phe Tyr Gly His Ile Gly Ala Met Asp Thr Met Ala Leu Ala Leu Lys
                355                 360                 365

Ile Ala Ala Arg Met Ile Glu Asp Gly Glu Leu Asp Lys Arg Ile Ala
                370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
                405                 410                 415

Leu Ser Pro Val His Gln Ser Gly Arg Gln Glu Gln Leu Glu Asn Leu
                420                 425                 430

Val Asn His Tyr Leu Phe Asp Lys
                435                 440

<210> SEQ ID NO 3
<211> LENGTH: 1455
<212> TYPE: DNA
<213> ORGANISM: Escherichia coli
<220> FEATURE:
<221> NAME/KEY: CDS
<222> LOCATION: (1)..(1455)

<400> SEQUENCE: 3 atg tat atc ggg ata gat ctt ggc acc tcg ggc gta aaa gtt att ttg        48
Met Tyr Ile Gly Ile Asp Leu Gly Thr Ser Gly Val Lys Val Ile Leu
 1               5                  10                  15 ctc aac gag cag ggt gag gtg gtt gct gcg caa acg gaa aag ctg acc        96
Leu Asn Glu Gln Gly Glu Val Val Ala Ala Gln Thr Glu Lys Leu Thr
                20                  25                  30 gtt tcg cgc ccg cat cca ctc tgg tcg gaa caa gac ccg gaa cag tgg       144
Val Ser Arg Pro His Pro Leu Trp Ser Glu Gln Asp Pro Glu Gln Trp
```

```
                  35                  40                  45
tgg cag gca act gat cgc gca atg aaa gct ctg ggc gat cag cat tct    192
Trp Gln Ala Thr Asp Arg Ala Met Lys Ala Leu Gly Asp Gln His Ser
     50                  55                  60 ctg cag gac gtt aaa gca ttg ggt att gcc ggc cag atg cac gga gca    240
Leu Gln Asp Val Lys Ala Leu Gly Ile Ala Gly Gln Met His Gly Ala
 65                  70                  75                  80 acc ttg ctg gat gct cag caa cgg gtg tta cgc cct gcc att ttg tgg    288
Thr Leu Leu Asp Ala Gln Gln Arg Val Leu Arg Pro Ala Ile Leu Trp
                 85                  90                  95 aac gac ggg cgc tgt gcg caa gag tgc act ttg ctg gaa gcg cga gtt    336
Asn Asp Gly Arg Cys Ala Gln Glu Cys Thr Leu Leu Glu Ala Arg Val
            100                 105                 110 ccg caa tcg cgg gtg att acc ggc aac ctg atg atg ccc gga ttt act    384
Pro Gln Ser Arg Val Ile Thr Gly Asn Leu Met Met Pro Gly Phe Thr
        115                 120                 125 gcg cct aaa ttg cta tgg gtt cag cgg cat gag ccg gag ata ttc cgt    432
Ala Pro Lys Leu Leu Trp Val Gln Arg His Glu Pro Glu Ile Phe Arg
    130                 135                 140 caa atc gac aaa gta tta tta ccg aaa gat tac ttg cgt ctg cgt atg    480
Gln Ile Asp Lys Val Leu Leu Pro Lys Asp Tyr Leu Arg Leu Arg Met
145                 150                 155                 160 acg ggg gag ttt gcc agc gat atg tct gac gca gct ggc acc atg tgg    528
Thr Gly Glu Phe Ala Ser Asp Met Ser Asp Ala Ala Gly Thr Met Trp
                165                 170                 175 ctg gat gtc gca aag cgt gac tgg agt gac gtc atg ctg cag gct tgc    576
Leu Asp Val Ala Lys Arg Asp Trp Ser Asp Val Met Leu Gln Ala Cys
            180                 185                 190 gac tta tct cgt gac cag atg ccc gca tta tac gaa ggc agc gaa att    624
Asp Leu Ser Arg Asp Gln Met Pro Ala Leu Tyr Glu Gly Ser Glu Ile
        195                 200                 205 act ggt gct ttg tta cct gaa gtt gcg aaa gcg tgg ggt atg gcg acg    672
Thr Gly Ala Leu Leu Pro Glu Val Ala Lys Ala Trp Gly Met Ala Thr
    210                 215                 220 gtg cca gtt gtc gca ggc ggt ggc gac aat gca gct ggt gca gtt ggt    720
Val Pro Val Val Ala Gly Gly Gly Asp Asn Ala Ala Gly Ala Val Gly
225                 230                 235                 240 gtg gga atg gtt gat gct aat cag gca atg tta tcg ctg ggg acg tcg    768
Val Gly Met Val Asp Ala Asn Gln Ala Met Leu Ser Leu Gly Thr Ser
                245                 250                 255 ggg gtc tat ttt gct gtc agc gaa ggg ttc tta agc aag cca gaa agc    816
Gly Val Tyr Phe Ala Val Ser Glu Gly Phe Leu Ser Lys Pro Glu Ser
            260                 265                 270 gcc gta cat agc ttt tgc cat gcg cta ccg caa cgt tgg cat tta atg    864
Ala Val His Ser Phe Cys His Ala Leu Pro Gln Arg Trp His Leu Met
        275                 280                 285 tct gtg atg ctg agt gca gcg tcg tgt ctg gat tgg gcc gcg aaa tta    912
Ser Val Met Leu Ser Ala Ala Ser Cys Leu Asp Trp Ala Ala Lys Leu
    290                 295                 300 acc ggc ctg agc aat gtc cca gct tta atc gct gca gct caa cag gct    960
Thr Gly Leu Ser Asn Val Pro Ala Leu Ile Ala Ala Ala Gln Gln Ala
305                 310                 315                 320 gat gaa agt gcc gag cca gtt tgg ttt ctg cct tat ctt tcc ggc gag   1008
Asp Glu Ser Ala Glu Pro Val Trp Phe Leu Pro Tyr Leu Ser Gly Glu
                325                 330                 335 cgt acg cca cac aat aat ccc cag gcg aag ggg gtt ttc ttt ggt ttg   1056
Arg Thr Pro His Asn Asn Pro Gln Ala Lys Gly Val Phe Phe Gly Leu
            340                 345                 350 act cat caa cat ggc ccc aat gaa ctg gcg cga gca gtg ctg gaa ggc   1104
Thr His Gln His Gly Pro Asn Glu Leu Ala Arg Ala Val Leu Glu Gly
```

```
                355                 360                 365
gtg ggt tat gcg ctg gca gat ggc atg gat gtc gtg cat gcc tgc ggt    1152
Val Gly Tyr Ala Leu Ala Asp Gly Met Asp Val Val His Ala Cys Gly
    370                 375                 380 att aaa ccg caa agt gtt acg ttg att ggg ggc ggg gcg cgt agt gag    1200
Ile Lys Pro Gln Ser Val Thr Leu Ile Gly Gly Gly Ala Arg Ser Glu
385                 390                 395                 400 tac tgg cgt cag atg ctg gcg gat atc agc ggt cag cag ctc gat tac    1248
Tyr Trp Arg Gln Met Leu Ala Asp Ile Ser Gly Gln Gln Leu Asp Tyr
                405                 410                 415 cgt acg ggg ggg gat gtg ggg cca gca ctg ggc gca gca agg ctg gcg    1296
Arg Thr Gly Gly Asp Val Gly Pro Ala Leu Gly Ala Ala Arg Leu Ala
        420                 425                 430 cag atc gcg gcg aat cca gag aaa tcg ctc att gaa ttg ttg ccg caa    1344
Gln Ile Ala Ala Asn Pro Glu Lys Ser Leu Ile Glu Leu Leu Pro Gln
            435                 440                 445 cta ccg tta gaa cag tcg cat cta cca gat gcg cag cgt tat gcc gct    1392
Leu Pro Leu Glu Gln Ser His Leu Pro Asp Ala Gln Arg Tyr Ala Ala
    450                 455                 460 tat cag cca cga cga gaa acg ttc cgt cgc ctc tat cag caa ctt ctg    1440
Tyr Gln Pro Arg Arg Glu Thr Phe Arg Arg Leu Tyr Gln Gln Leu Leu
465                 470                 475                 480 cca tta atg gcg taa                                                1455
Pro Leu Met Ala <210> SEQ ID NO 4
<211> LENGTH: 484
<212> TYPE: PRT
<213> ORGANISM: Escherichia coli

<400> SEQUENCE: 4

Met Tyr Ile Gly Ile Asp Leu Gly Thr Ser Gly Val Lys Val Ile Leu
  1               5                  10                  15

Leu Asn Glu Gln Gly Glu Val Val Ala Ala Gln Thr Glu Lys Leu Thr
             20                  25                  30

Val Ser Arg Pro His Pro Leu Trp Ser Glu Gln Asp Pro Glu Gln Trp
         35                  40                  45

Trp Gln Ala Thr Asp Arg Ala Met Lys Ala Leu Gly Asp Gln His Ser
     50                  55                  60

Leu Gln Asp Val Lys Ala Leu Gly Ile Ala Gly Gln Met His Gly Ala
 65                  70                  75                  80

Thr Leu Leu Asp Ala Gln Gln Arg Val Leu Arg Pro Ala Ile Leu Trp
                 85                  90                  95

Asn Asp Gly Arg Cys Ala Gln Glu Cys Thr Leu Leu Glu Ala Arg Val
            100                 105                 110

Pro Gln Ser Arg Val Ile Thr Gly Asn Leu Met Met Pro Gly Phe Thr
        115                 120                 125

Ala Pro Lys Leu Leu Trp Val Gln Arg His Glu Pro Glu Ile Phe Arg
    130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
        195                 200                 205
```

```
Thr Gly Ala Leu Leu Pro Glu Val Ala Lys Ala Trp Gly Met Ala Thr
    210                 215                 220
Val Pro Val Val Ala Gly Gly Asp Asn Ala Ala Gly Ala Val Gly
225                 230                 235                 240
Val Gly Met Val Asp Ala Asn Gln Ala Met Leu Ser Leu Gly Thr Ser
                    245                 250                 255
Gly Val Tyr Phe Ala Val Ser Glu Gly Phe Leu Ser Lys Pro Glu Ser
                260                 265                 270
Ala Val His Ser Phe Cys His Ala Leu Pro Gln Arg Trp His Leu Met
                275                 280                 285
Ser Val Met Leu Ser Ala Ala Ser Cys Leu Asp Trp Ala Ala Lys Leu
            290                 295                 300
Thr Gly Leu Ser Asn Val Pro Ala Leu Ile Ala Ala Gln Gln Ala
305                 310                 315                 320
Asp Glu Ser Ala Glu Pro Val Trp Phe Leu Pro Tyr Leu Ser Gly Glu
                    325                 330                 335
Arg Thr Pro His Asn Asn Pro Gln Ala Lys Gly Val Phe Phe Gly Leu
                340                 345                 350
Thr His Gln His Gly Pro Asn Glu Leu Ala Arg Ala Val Leu Glu Gly
            355                 360                 365
Val Gly Tyr Ala Leu Ala Asp Gly Met Asp Val Val His Ala Cys Gly
370                 375                 380
Ile Lys Pro Gln Ser Val Thr Leu Ile Gly Gly Gly Ala Arg Ser Glu
385                 390                 395                 400
Tyr Trp Arg Gln Met Leu Ala Asp Ile Ser Gly Gln Gln Leu Asp Tyr
                    405                 410                 415
Arg Thr Gly Gly Asp Val Gly Pro Ala Leu Gly Ala Ala Arg Leu Ala
                420                 425                 430
Gln Ile Ala Ala Asn Pro Glu Lys Ser Leu Ile Glu Leu Leu Pro Gln
            435                 440                 445
Leu Pro Leu Glu Gln Ser His Leu Pro Asp Ala Gln Arg Tyr Ala Ala
            450                 455                 460
Tyr Gln Pro Arg Arg Glu Thr Phe Arg Arg Leu Tyr Gln Gln Leu Leu
465                 470                 475                 480
Pro Leu Met Ala

<210> SEQ ID NO 5
<211> LENGTH: 993
<212> TYPE: DNA
<213> ORGANISM: Escherichia coli
<220> FEATURE:
<221> NAME/KEY: CDS
<222> LOCATION: (1)..(993)

<400> SEQUENCE: 5 atg aaa ata aag aac att cta ctc acc ctt tgc acc tca ctc ctg ctt      48
Met Lys Ile Lys Asn Ile Leu Leu Thr Leu Cys Thr Ser Leu Leu Leu
  1               5                  10                  15 acc aac gtt gct gca cac gcc aaa gaa gtc aaa ata ggt atg gcg att      96
Thr Asn Val Ala Ala His Ala Lys Glu Val Lys Ile Gly Met Ala Ile
             20                  25                  30 gat gat ctc cgt ctt gaa cgc tgg caa aaa gat cga gat atc ttt gtg     144
Asp Asp Leu Arg Leu Glu Arg Trp Gln Lys Asp Arg Asp Ile Phe Val
         35                  40                  45 aaa aag gca gaa tct ctc ggc gcg aaa gta ttt gta cag tct gca aat     192
Lys Lys Ala Glu Ser Leu Gly Ala Lys Val Phe Val Gln Ser Ala Asn
     50                  55                  60
```

| | | |
|---|---|---|
| ggc aat gaa gaa aca caa atg tcg cag att gaa aac atg ata aac cgg<br>Gly Asn Glu Glu Thr Gln Met Ser Gln Ile Glu Asn Met Ile Asn Arg<br>65                        70                      75                      80 | 240 |
| ggt gtc gat gtt ctt gtc att att ccg tat aac ggt cag gta tta agt<br>Gly Val Asp Val Leu Val Ile Ile Pro Tyr Asn Gly Gln Val Leu Ser<br>                      85                      90                      95 | 288 |
| aac gtt gta aaa gaa gcc aaa caa gaa ggc att aaa gta tta gct tac<br>Asn Val Val Lys Glu Ala Lys Gln Glu Gly Ile Lys Val Leu Ala Tyr<br>                100                     105                     110 | 336 |
| gac cgt atg att aac gat gcg gat atc gat ttt tat att tct ttc gat<br>Asp Arg Met Ile Asn Asp Ala Asp Ile Asp Phe Tyr Ile Ser Phe Asp<br>             115                     120                     125 | 384 |
| aac gaa aaa gtc ggt gaa ctg cag gca aaa gcc ctg gtc gat att gtt<br>Asn Glu Lys Val Gly Glu Leu Gln Ala Lys Ala Leu Val Asp Ile Val<br>130                       135                     140 | 432 |
| ccg caa ggt aat tac ttc ctg atg ggc ggc tcg ccg gta gat aac aac<br>Pro Gln Gly Asn Tyr Phe Leu Met Gly Gly Ser Pro Val Asp Asn Asn<br>145                       150                     155                    160 | 480 |
| gcc aag ctg ttc cgc gcc gga caa atg aaa gtg tta aaa cct tac gtt<br>Ala Lys Leu Phe Arg Ala Gly Gln Met Lys Val Leu Lys Pro Tyr Val<br>             165                     170                     175 | 528 |
| gat tcc gga aaa att aaa gtc gtt ggt gac caa tgg gtt gat ggc tgg<br>Asp Ser Gly Lys Ile Lys Val Val Gly Asp Gln Trp Val Asp Gly Trp<br>               180                     185                     190 | 576 |
| tta ccg gaa aac gca ttg aaa att atg gaa aac gcg cta acc gcc aat<br>Leu Pro Glu Asn Ala Leu Lys Ile Met Glu Asn Ala Leu Thr Ala Asn<br>             195                     200                     205 | 624 |
| aat aac aaa att gat gct gta gtt gcc tca aac gat gcc acc gca ggt<br>Asn Asn Lys Ile Asp Ala Val Val Ala Ser Asn Asp Ala Thr Ala Gly<br>210                       215                     220 | 672 |
| ggg gca att cag gca tta agc gcg caa ggt tta tca ggg aaa gta gca<br>Gly Ala Ile Gln Ala Leu Ser Ala Gln Gly Leu Ser Gly Lys Val Ala<br>225                       230                     235                    240 | 720 |
| atc tcc ggc cag gat gcg gat ctc gca ggt att aaa cgt att gct gcc<br>Ile Ser Gly Gln Asp Ala Asp Leu Ala Gly Ile Lys Arg Ile Ala Ala<br>             245                     250                     255 | 768 |
| ggt acg caa act atg acg gtg tat aaa cct att acg ttg ttg gca aat<br>Gly Thr Gln Thr Met Thr Val Tyr Lys Pro Ile Thr Leu Leu Ala Asn<br>               260                     265                     270 | 816 |
| act gcc gca gaa att gcc gtt gag ttg ggc aat ggt cag gaa cca aaa<br>Thr Ala Ala Glu Ile Ala Val Glu Leu Gly Asn Gly Gln Glu Pro Lys<br>             275                     280                     285 | 864 |
| gca gat acc aca ctg aat aat ggc ctg aaa gat gtc ccc tcc cgc ctc<br>Ala Asp Thr Thr Leu Asn Asn Gly Leu Lys Asp Val Pro Ser Arg Leu<br>290                       295                     300 | 912 |
| ctg aca ccg atc gat gtg aat aaa aac aac atc aaa gat acg gta att<br>Leu Thr Pro Ile Asp Val Asn Lys Asn Asn Ile Lys Asp Thr Val Ile<br>305                       310                     315                    320 | 960 |
| aaa gac gga ttc cac aaa gag agc gag ctg taa<br>Lys Asp Gly Phe His Lys Glu Ser Glu Leu<br>             325                     330 | 993 |

<210> SEQ ID NO 6
<211> LENGTH: 330
<212> TYPE: PRT
<213> ORGANISM: Escherichia coli

<400> SEQUENCE: 6

Met Lys Ile Lys Asn Ile Leu Leu Thr Leu Cys Thr Ser Leu Leu Leu
1                   5                     10                     15

Thr Asn Val Ala Ala His Ala Lys Glu Val Lys Ile Gly Met Ala Ile

```
                20                  25                  30
Asp Asp Leu Arg Leu Glu Arg Trp Gln Lys Asp Arg Asp Ile Phe Val
            35                  40                  45

Lys Lys Ala Glu Ser Leu Gly Ala Lys Val Phe Val Gln Ser Ala Asn
    50                  55                  60

Gly Asn Glu Glu Thr Gln Met Ser Gln Ile Glu Asn Met Ile Asn Arg
65                  70                  75                  80

Gly Val Asp Val Leu Val Ile Ile Pro Tyr Asn Gly Gln Val Leu Ser
                85                  90                  95

Asn Val Val Lys Glu Ala Lys Gln Gly Ile Lys Val Leu Ala Tyr
            100                 105                 110

Asp Arg Met Ile Asn Asp Ala Asp Ile Asp Phe Tyr Ile Ser Phe Asp
        115                 120                 125

Asn Glu Lys Val Gly Glu Leu Gln Ala Lys Ala Leu Val Asp Ile Val
130                 135                 140

Pro Gln Gly Asn Tyr Phe Leu Met Gly Gly Ser Pro Val Asp Asn Asn
145                 150                 155                 160

Ala Lys Leu Phe Arg Ala Gly Gln Met Lys Val Leu Lys Pro Tyr Val
                165                 170                 175

Asp Ser Gly Lys Ile Lys Val Val Gly Asp Gln Trp Val Asp Gly Trp
            180                 185                 190

Leu Pro Glu Asn Ala Leu Lys Ile Met Glu Asn Ala Leu Thr Ala Asn
        195                 200                 205

Asn Asn Lys Ile Asp Ala Val Val Ala Ser Asn Asp Ala Thr Ala Gly
    210                 215                 220

Gly Ala Ile Gln Ala Leu Ser Ala Gln Gly Leu Ser Gly Lys Val Ala
225                 230                 235                 240

Ile Ser Gly Gln Asp Ala Asp Leu Ala Gly Ile Lys Arg Ile Ala Ala
                245                 250                 255

Gly Thr Gln Thr Met Thr Val Tyr Lys Pro Ile Thr Leu Leu Ala Asn
            260                 265                 270

Thr Ala Ala Glu Ile Ala Val Glu Leu Gly Asn Gly Gln Glu Pro Lys
        275                 280                 285

Ala Asp Thr Thr Leu Asn Asn Gly Leu Lys Asp Val Pro Ser Arg Leu
    290                 295                 300

Leu Thr Pro Ile Asp Val Asn Lys Asn Asn Ile Lys Asp Thr Val Ile
305                 310                 315                 320

Lys Asp Gly Phe His Lys Glu Ser Glu Leu
                325                 330

<210> SEQ ID NO 7
<211> LENGTH: 1542
<212> TYPE: DNA
<213> ORGANISM: Escherichia coli
<220> FEATURE:
<221> NAME/KEY: CDS
<222> LOCATION: (1)..(1542)

<400> SEQUENCE: 7 atg cct tat cta ctt gaa atg aag aac att acc aaa acc ttc ggc agt    48
Met Pro Tyr Leu Leu Glu Met Lys Asn Ile Thr Lys Thr Phe Gly Ser
1               5                   10                  15 gtg aag gcg att gat aac gtc tgc ttg cgg ttg aat gct ggc gaa atc    96
Val Lys Ala Ile Asp Asn Val Cys Leu Arg Leu Asn Ala Gly Glu Ile
                20                  25                  30 gtc tca ctt tgt ggg gaa aat ggg tct ggt aaa tca acg ctg atg aaa   144
Val Ser Leu Cys Gly Glu Asn Gly Ser Gly Lys Ser Thr Leu Met Lys
```

```
              35                  40                  45
gtg ctg tgt ggt att tat ccc cat ggc tcc tac gaa ggc gaa att att    192
Val Leu Cys Gly Ile Tyr Pro His Gly Ser Tyr Glu Gly Glu Ile Ile
     50                  55                  60 ttt gcg gga gaa gag att cag gcg agt cac atc cgc gat acc gaa cgc    240
Phe Ala Gly Glu Glu Ile Gln Ala Ser His Ile Arg Asp Thr Glu Arg
 65                  70                  75                  80 aaa ggt atc gcc atc att cat cag gaa ttg gcc ctg gtg aaa gaa ttg    288
Lys Gly Ile Ala Ile Ile His Gln Glu Leu Ala Leu Val Lys Glu Leu
                 85                  90                  95 acc gtg ctg gaa aat atc ttc ctg ggt aac gaa ata acc cac aat ggc    336
Thr Val Leu Glu Asn Ile Phe Leu Gly Asn Glu Ile Thr His Asn Gly
            100                 105                 110 att atg gat tat gac ctg atg acg cta cgc tgt cag aag ctg ctc gca    384
Ile Met Asp Tyr Asp Leu Met Thr Leu Arg Cys Gln Lys Leu Leu Ala
        115                 120                 125 cag gtc agt tta tcc att tca cct gat acc cgc gtt ggc gat tta ggg    432
Gln Val Ser Leu Ser Ile Ser Pro Asp Thr Arg Val Gly Asp Leu Gly
    130                 135                 140 ctt ggg caa caa caa ctg gtt gaa att gcc aag gca ctt aat aaa cag    480
Leu Gly Gln Gln Gln Leu Val Glu Ile Ala Lys Ala Leu Asn Lys Gln
145                 150                 155                 160 gtg cgc ttg tta att ctc gat gaa ccg aca gcc tca tta act gag cag    528
Val Arg Leu Leu Ile Leu Asp Glu Pro Thr Ala Ser Leu Thr Glu Gln
                165                 170                 175 gaa acg tcg att tta ctg gat att att cgc gat cta caa cag cac ggt    576
Glu Thr Ser Ile Leu Leu Asp Ile Ile Arg Asp Leu Gln Gln His Gly
            180                 185                 190 atc gcc tgt att tat att tcg cac aaa ctc aac gaa gtc aaa gcg att    624
Ile Ala Cys Ile Tyr Ile Ser His Lys Leu Asn Glu Val Lys Ala Ile
        195                 200                 205 tcc gat acg att tgc gtt att cgc gac gga cag cac att ggt acg cgt    672
Ser Asp Thr Ile Cys Val Ile Arg Asp Gly Gln His Ile Gly Thr Arg
    210                 215                 220 gat gct gcc gga atg agt gaa gac gat att atc acc atg atg gtc ggg    720
Asp Ala Ala Gly Met Ser Glu Asp Asp Ile Ile Thr Met Met Val Gly
225                 230                 235                 240 cga gag tta acc gcg ctt tac cct aat gaa cca cat acc acc gga gat    768
Arg Glu Leu Thr Ala Leu Tyr Pro Asn Glu Pro His Thr Thr Gly Asp
                245                 250                 255 gaa ata tta cgt att gaa cat ctg acg gca tgg cat ccg gtt aat cgt    816
Glu Ile Leu Arg Ile Glu His Leu Thr Ala Trp His Pro Val Asn Arg
            260                 265                 270 cat att aaa cga gtt aat gat gtc tcg ttt tcc ctg aaa cgt ggc gaa    864
His Ile Lys Arg Val Asn Asp Val Ser Phe Ser Leu Lys Arg Gly Glu
        275                 280                 285 ata ttg ggt att gcc gga ctc gtt ggt gcc gga cgt acc gag acc att    912
Ile Leu Gly Ile Ala Gly Leu Val Gly Ala Gly Arg Thr Glu Thr Ile
    290                 295                 300 cag tgc ctg ttt ggt gtg tgg ccc gga caa tgg gaa gga aaa att tat    960
Gln Cys Leu Phe Gly Val Trp Pro Gly Gln Trp Glu Gly Lys Ile Tyr
305                 310                 315                 320 att gat ggc aaa cag gta gat att cgt aac tgt cag caa gcc atc gcc   1008
Ile Asp Gly Lys Gln Val Asp Ile Arg Asn Cys Gln Gln Ala Ile Ala
                325                 330                 335 cag ggg att gcg atg gtc ccc gaa gac aga aag cgc gac ggc atc gtt   1056
Gln Gly Ile Ala Met Val Pro Glu Asp Arg Lys Arg Asp Gly Ile Val
            340                 345                 350 ccg gta atg gcg gtt ggt aaa aat att acc ctc gcc gca ctc aat aaa   1104
Pro Val Met Ala Val Gly Lys Asn Ile Thr Leu Ala Ala Leu Asn Lys
```

```
                355                 360                 365
ttt acc ggt ggc att agc cag ctt gat gac gcg gca gag caa aaa tgt      1152
Phe Thr Gly Gly Ile Ser Gln Leu Asp Asp Ala Ala Glu Gln Lys Cys
370                 375                 380 att ctg gaa tca atc cag caa ctc aaa gtt aaa acg tcg tcc ccc gac      1200
Ile Leu Glu Ser Ile Gln Gln Leu Lys Val Lys Thr Ser Ser Pro Asp
385                 390                 395                 400 ctt gct att gga cgt ttg agc ggc ggc aat cag caa aaa gcg atc ctc      1248
Leu Ala Ile Gly Arg Leu Ser Gly Gly Asn Gln Gln Lys Ala Ile Leu
                405                 410                 415 gct cgc tgt ctg tta ctt aac ccg cgc att ctc att ctt gat gaa ccc      1296
Ala Arg Cys Leu Leu Leu Asn Pro Arg Ile Leu Ile Leu Asp Glu Pro
        420                 425                 430 acc agg ggt atc gat att ggc gcg aaa tac gag atc tac aaa tta att      1344
Thr Arg Gly Ile Asp Ile Gly Ala Lys Tyr Glu Ile Tyr Lys Leu Ile
            435                 440                 445 aac caa ctc gtc cag cag ggt att gcc gtt att gtc atc tct tcc gaa      1392
Asn Gln Leu Val Gln Gln Gly Ile Ala Val Ile Val Ile Ser Ser Glu
450                 455                 460 tta cct gaa gtg ctc ggc ctt agc gat cgt gta ctg gtg atg cat gaa      1440
Leu Pro Glu Val Leu Gly Leu Ser Asp Arg Val Leu Val Met His Glu
465                 470                 475                 480 ggg aaa cta aaa gcc aac ctg ata aat cat aac ctg act cag gag cag      1488
Gly Lys Leu Lys Ala Asn Leu Ile Asn His Asn Leu Thr Gln Glu Gln
                485                 490                 495 gtg atg gaa gcc gca ttg agg agc gaa cat cat gtc gaa aag caa tcc      1536
Val Met Glu Ala Ala Leu Arg Ser Glu His His Val Glu Lys Gln Ser
        500                 505                 510 gtc tga                                                              1542
Val

<210> SEQ ID NO 8
<211> LENGTH: 513
<212> TYPE: PRT
<213> ORGANISM: Escherichia coli

<400> SEQUENCE: 8

Met Pro Tyr Leu Leu Glu Met Lys Asn Ile Thr Lys Thr Phe Gly Ser
 1               5                  10                  15

Val Lys Ala Ile Asp Asn Val Cys Leu Arg Leu Asn Ala Gly Glu Ile
            20                  25                  30

Val Ser Leu Cys Gly Glu Asn Gly Ser Gly Lys Ser Thr Leu Met Lys
        35                  40                  45

Val Leu Cys Gly Ile Tyr Pro His Gly Ser Tyr Glu Gly Glu Ile Ile
    50                  55                  60

Phe Ala Gly Glu Glu Ile Gln Ala Ser His Ile Arg Asp Thr Glu Arg
65                  70                  75                  80

Lys Gly Ile Ala Ile Ile His Gln Glu Leu Ala Leu Val Lys Glu Leu
                85                  90                  95

Thr Val Leu Glu Asn Ile Phe Leu Gly Asn Glu Ile Thr His Asn Gly
            100                 105                 110

Ile Met Asp Tyr Asp Leu Met Thr Leu Arg Cys Gln Lys Leu Leu Ala
        115                 120                 125

Gln Val Ser Leu Ser Ile Ser Pro Asp Thr Arg Val Gly Asp Leu Gly
    130                 135                 140

Leu Gly Gln Gln Gln Leu Val Glu Ile Ala Lys Ala Leu Asn Lys Gln
145                 150                 155                 160

Val Arg Leu Leu Ile Leu Asp Glu Pro Thr Ala Ser Leu Thr Glu Gln
```

-continued

```
                    165                 170                 175
Glu Thr Ser Ile Leu Leu Asp Ile Ile Arg Asp Leu Gln Gln His Gly
                180                 185                 190
Ile Ala Cys Ile Tyr Ile Ser His Lys Leu Asn Glu Val Lys Ala Ile
                195                 200                 205
Ser Asp Thr Ile Cys Val Ile Arg Asp Gly Gln His Ile Gly Thr Arg
            210                 215                 220
Asp Ala Ala Gly Met Ser Glu Asp Ile Ile Thr Met Met Val Gly
225                 230                 235                 240
Arg Glu Leu Thr Ala Leu Tyr Pro Asn Glu Pro His Thr Thr Gly Asp
                245                 250                 255
Glu Ile Leu Arg Ile Glu His Leu Thr Ala Trp His Pro Val Asn Arg
                260                 265                 270
His Ile Lys Arg Val Asn Asp Val Ser Phe Ser Leu Lys Arg Gly Glu
            275                 280                 285
Ile Leu Gly Ile Ala Gly Leu Val Gly Ala Gly Arg Thr Glu Thr Ile
            290                 295                 300
Gln Cys Leu Phe Gly Val Trp Pro Gly Gln Trp Glu Gly Lys Ile Tyr
305                 310                 315                 320
Ile Asp Gly Lys Gln Val Asp Ile Arg Asn Cys Gln Gln Ala Ile Ala
                325                 330                 335
Gln Gly Ile Ala Met Val Pro Glu Asp Arg Lys Arg Asp Gly Ile Val
                340                 345                 350
Pro Val Met Ala Val Gly Lys Asn Ile Thr Leu Ala Ala Leu Asn Lys
                355                 360                 365
Phe Thr Gly Gly Ile Ser Gln Leu Asp Ala Ala Glu Gln Lys Cys
            370                 375                 380
Ile Leu Glu Ser Ile Gln Gln Leu Lys Val Lys Thr Ser Ser Pro Asp
385                 390                 395                 400
Leu Ala Ile Gly Arg Leu Ser Gly Gly Asn Gln Gln Lys Ala Ile Leu
                405                 410                 415
Ala Arg Cys Leu Leu Leu Asn Pro Arg Ile Leu Ile Leu Asp Glu Pro
                420                 425                 430
Thr Arg Gly Ile Asp Ile Gly Ala Lys Tyr Glu Ile Tyr Lys Leu Ile
            435                 440                 445
Asn Gln Leu Val Gln Gln Gly Ile Ala Val Ile Val Ile Ser Ser Glu
            450                 455                 460
Leu Pro Glu Val Leu Gly Leu Ser Asp Arg Val Leu Val Met His Glu
465                 470                 475                 480
Gly Lys Leu Lys Ala Asn Leu Ile Asn His Asn Leu Thr Gln Glu Gln
                485                 490                 495
Val Met Glu Ala Ala Leu Arg Ser Glu His His Val Glu Lys Gln Ser
                500                 505                 510
Val
```

<210> SEQ ID NO 9
<211> LENGTH: 1182
<212> TYPE: DNA
<213> ORGANISM: Escherichia coli
<220> FEATURE:
<221> NAME/KEY: CDS
<222> LOCATION: (1)..(1182)

<400> SEQUENCE: 9

```
atg tcg aaa agc aat ccg tct gaa gtg aaa ttg gcc gta ccg aca tcc      48
Met Ser Lys Ser Asn Pro Ser Glu Val Lys Leu Ala Val Pro Thr Ser
```

```
           1               5              10              15 ggt ggc ttc tcc ggg ctg aaa tca ctg aat ttg cag gtc ttc gtg atg      96
Gly Gly Phe Ser Gly Leu Lys Ser Leu Asn Leu Gln Val Phe Val Met
                 20              25              30 att gca gct atc atc gca atc atg ctg ttc ttt acc tgg acc acc gat     144
Ile Ala Ala Ile Ile Ala Ile Met Leu Phe Phe Thr Trp Thr Thr Asp
             35              40              45 ggt gcc tac tta agc gcc cgt aac gtc tcc aac ctg tta cgc cag acc     192
Gly Ala Tyr Leu Ser Ala Arg Asn Val Ser Asn Leu Leu Arg Gln Thr
         50              55              60 gcg att acc ggc atc ctc gcg gta gga atg gtg ttc gtc ata att tct     240
Ala Ile Thr Gly Ile Leu Ala Val Gly Met Val Phe Val Ile Ile Ser
 65              70              75              80 gct gaa atc gac ctt tcc gtc ggc tca atg atg ggg ctg tta ggt ggc     288
Ala Glu Ile Asp Leu Ser Val Gly Ser Met Met Gly Leu Leu Gly Gly
                 85              90              95 gtc gcg gcg att tgt gac gtc tgg tta ggc tgg cct ttg cca ctt acc     336
Val Ala Ala Ile Cys Asp Val Trp Leu Gly Trp Pro Leu Pro Leu Thr
             100             105             110 atc att gtg acg ctg gtt ctg gga ctg ctc ctc ggt gcc tgg aac gga     384
Ile Ile Val Thr Leu Val Leu Gly Leu Leu Leu Gly Ala Trp Asn Gly
         115             120             125 tgg tgg gtc gcg tac cgt aaa gtc cct tca ttt att gtc acc ctc gcg     432
Trp Trp Val Ala Tyr Arg Lys Val Pro Ser Phe Ile Val Thr Leu Ala
 130             135             140 ggc atg ttg gca ttt cgc ggc ata ctc att ggc atc acc aac ggc acg     480
Gly Met Leu Ala Phe Arg Gly Ile Leu Ile Gly Ile Thr Asn Gly Thr
145             150             155             160 act gta tcc ccc acc agc gcc gcg atg tca caa att ggg caa agc tat     528
Thr Val Ser Pro Thr Ser Ala Ala Met Ser Gln Ile Gly Gln Ser Tyr
                 165             170             175 ctc ccc gcc agt acc ggc ttc atc att ggc gcg ctt ggc tta atg gct     576
Leu Pro Ala Ser Thr Gly Phe Ile Ile Gly Ala Leu Gly Leu Met Ala
             180             185             190 ttt gtt ggt tgg caa tgg cgc gga aga atg cgc cgt cag gct ttg ggt     624
Phe Val Gly Trp Gln Trp Arg Gly Arg Met Arg Arg Gln Ala Leu Gly
         195             200             205 tta cag tct ccg gcc tct acc gca gta gtc ggt cgc cag gct tta acc     672
Leu Gln Ser Pro Ala Ser Thr Ala Val Val Gly Arg Gln Ala Leu Thr
 210             215             220 gct atc atc gta tta ggc gca atc tgg ctg ttg aat gat tac cgt ggc     720
Ala Ile Ile Val Leu Gly Ala Ile Trp Leu Leu Asn Asp Tyr Arg Gly
225             230             235             240 gtt ccc act cct gtt ctg ctg acg ttg ctg tta ctc ggc gga atg         768
Val Pro Thr Pro Val Leu Leu Thr Leu Leu Leu Gly Gly Met
                 245             250             255 ttt atg gca acg cgg acg gca ttt gga cga cgc att tat gcc atc ggc     816
Phe Met Ala Thr Arg Thr Ala Phe Gly Arg Arg Ile Tyr Ala Ile Gly
             260             265             270 ggc aat ctg gaa gca gca cgt ctc tcc ggg att aac gtt gaa cgc acc     864
Gly Asn Leu Glu Ala Ala Arg Leu Ser Gly Ile Asn Val Glu Arg Thr
         275             280             285 aaa ctt gcc gtg ttc gcg att aac gga tta atg gta gcc atc gcc gga     912
Lys Leu Ala Val Phe Ala Ile Asn Gly Leu Met Val Ala Ile Ala Gly
 290             295             300 tta atc ctt agt tct cga ctt ggc gct ggt tca cct tct gcg gga aat     960
Leu Ile Leu Ser Ser Arg Leu Gly Ala Gly Ser Pro Ser Ala Gly Asn
305             310             315             320 atc gcc gaa ctg gac gca att gca gca tgc gtg att ggc ggc acc agc    1008
Ile Ala Glu Leu Asp Ala Ile Ala Ala Cys Val Ile Gly Gly Thr Ser
```

```
                    325                 330                 335
ctg gct ggc ggt gtg gga agc gtt gcc gga gca gta atg ggg gca ttt    1056
Leu Ala Gly Gly Val Gly Ser Val Ala Gly Ala Val Met Gly Ala Phe
            340                 345                 350 atc atg gct tca ctg gat aac ggc atg agt atg atg gat gta ccg acc    1104
Ile Met Ala Ser Leu Asp Asn Gly Met Ser Met Met Asp Val Pro Thr
        355                 360                 365 ttc tgg cag tat atc gtt aaa ggt gcg att ctg ttg ctg gca gta tgg    1152
Phe Trp Gln Tyr Ile Val Lys Gly Ala Ile Leu Leu Leu Ala Val Trp
370                 375                 380 atg gac tcc gca acc aaa cgc cgt tct tga                            1182
Met Asp Ser Ala Thr Lys Arg Arg Ser
385                 390

<210> SEQ ID NO 10
<211> LENGTH: 393
<212> TYPE: PRT
<213> ORGANISM: Escherichia coli

<400> SEQUENCE: 10

Met Ser Lys Ser Asn Pro Ser Glu Val Lys Leu Ala Val Pro Thr Ser
1               5                   10                  15

Gly Gly Phe Ser Gly Leu Lys Ser Leu Asn Leu Gln Val Phe Val Met
            20                  25                  30

Ile Ala Ala Ile Ile Ala Ile Met Leu Phe Phe Thr Trp Thr Thr Asp
        35                  40                  45

Gly Ala Tyr Leu Ser Ala Arg Asn Val Ser Asn Leu Leu Arg Gln Thr
    50                  55                  60

Ala Ile Thr Gly Ile Leu Ala Val Gly Met Val Phe Val Ile Ile Ser
65                  70                  75                  80

Ala Glu Ile Asp Leu Ser Val Gly Ser Met Met Gly Leu Leu Gly Gly
                85                  90                  95

Val Ala Ala Ile Cys Asp Val Trp Leu Gly Trp Pro Leu Pro Leu Thr
            100                 105                 110

Ile Ile Val Thr Leu Val Leu Gly Leu Leu Gly Ala Trp Asn Gly
        115                 120                 125

Trp Trp Val Ala Tyr Arg Lys Val Pro Ser Phe Ile Val Thr Leu Ala
    130                 135                 140

Gly Met Leu Ala Phe Arg Gly Ile Leu Ile Gly Ile Thr Asn Gly Thr
145                 150                 155                 160

Thr Val Ser Pro Thr Ser Ala Ala Met Ser Gln Ile Gly Gln Ser Tyr
                165                 170                 175

Leu Pro Ala Ser Thr Gly Phe Ile Ile Gly Ala Leu Gly Leu Met Ala
            180                 185                 190

Phe Val Gly Trp Gln Trp Arg Gly Arg Met Arg Arg Gln Ala Leu Gly
        195                 200                 205

Leu Gln Ser Pro Ala Ser Thr Ala Val Val Gly Arg Gln Ala Leu Thr
    210                 215                 220

Ala Ile Ile Val Leu Gly Ala Ile Trp Leu Leu Asn Asp Tyr Arg Gly
225                 230                 235                 240

Val Pro Thr Pro Val Leu Leu Leu Thr Leu Leu Leu Gly Gly Met
                245                 250                 255

Phe Met Ala Thr Arg Thr Ala Phe Gly Arg Arg Ile Tyr Ala Ile Gly
            260                 265                 270

Gly Asn Leu Glu Ala Ala Arg Leu Ser Gly Ile Asn Val Glu Arg Thr
        275                 280                 285
```

```
Lys Leu Ala Val Phe Ala Ile Asn Gly Leu Met Val Ala Ile Ala Gly
            290                 295                 300

Leu Ile Leu Ser Ser Arg Leu Gly Ala Gly Ser Pro Ser Ala Gly Asn
305                 310                 315                 320

Ile Ala Glu Leu Asp Ala Ile Ala Ala Cys Val Ile Gly Gly Thr Ser
                325                 330                 335

Leu Ala Gly Gly Val Gly Ser Val Ala Gly Ala Val Met Gly Ala Phe
                340                 345                 350

Ile Met Ala Ser Leu Asp Asn Gly Met Ser Met Met Asp Val Pro Thr
            355                 360                 365

Phe Trp Gln Tyr Ile Val Lys Gly Ala Ile Leu Leu Ala Val Trp
370                 375                 380

Met Asp Ser Ala Thr Lys Arg Arg Ser
385                 390
```

<210> SEQ ID NO 11
<211> LENGTH: 1179
<212> TYPE: DNA
<213> ORGANISM: Escherichia coli
<220> FEATURE:
<221> NAME/KEY: CDS
<222> LOCATION: (1)..(1179)

<400> SEQUENCE: 11

```
atg ttt act aaa cgt cac cgc atc aca tta ctg ttc aat gcc aat aaa      48
Met Phe Thr Lys Arg His Arg Ile Thr Leu Leu Phe Asn Ala Asn Lys
1               5                   10                  15 gcc tat gac cgg cag gta gta gaa ggc gta ggg gaa tat tta cag gcg      96
Ala Tyr Asp Arg Gln Val Val Glu Gly Val Gly Glu Tyr Leu Gln Ala
                20                  25                  30 tca caa tcg gaa tgg gat att ttc att gaa gaa gat ttc cgc gcc cgc     144
Ser Gln Ser Glu Trp Asp Ile Phe Ile Glu Glu Asp Phe Arg Ala Arg
            35                  40                  45 att gat aaa atc aag gac tgg tta gga gat ggc gtc att gcc gac ttc     192
Ile Asp Lys Ile Lys Asp Trp Leu Gly Asp Gly Val Ile Ala Asp Phe
        50                  55                  60 gac gac aaa cag atc gag caa gcg ctg gct gat gtc gac gtc ccc att     240
Asp Asp Lys Gln Ile Glu Gln Ala Leu Ala Asp Val Asp Val Pro Ile
65                  70                  75                  80 gtt ggg gtt ggc ggc tcg tat cac ctt gca gaa agt tac cca ccc gtt     288
Val Gly Val Gly Gly Ser Tyr His Leu Ala Glu Ser Tyr Pro Pro Val
                85                  90                  95 cat tac att gcc acc gat aac tat gcg ctg gtt gaa agc gca ttt ttg     336
His Tyr Ile Ala Thr Asp Asn Tyr Ala Leu Val Glu Ser Ala Phe Leu
                100                 105                 110 cat tta aaa gag aaa ggc gtt aac cgc ttt gct ttt tat ggt ctt ccg     384
His Leu Lys Glu Lys Gly Val Asn Arg Phe Ala Phe Tyr Gly Leu Pro
            115                 120                 125 gaa tca agc ggc aaa cgt tgg gcc act gag cgc gaa tat gca ttt cgt     432
Glu Ser Ser Gly Lys Arg Trp Ala Thr Glu Arg Glu Tyr Ala Phe Arg
        130                 135                 140 cag ctt gtc gcc gaa gaa aag tat cgc gga gtg gtt tat cag ggg tta     480
Gln Leu Val Ala Glu Glu Lys Tyr Arg Gly Val Val Tyr Gln Gly Leu
145                 150                 155                 160 gaa acc gcg cca gag aac tgg caa cac gcg caa aat cgg ctg gca gac     528
Glu Thr Ala Pro Glu Asn Trp Gln His Ala Gln Asn Arg Leu Ala Asp
                165                 170                 175 tgg cta caa acg cta cca ccg caa acc ggg att att gcc gtt act gac     576
Trp Leu Gln Thr Leu Pro Pro Gln Thr Gly Ile Ile Ala Val Thr Asp
            180                 185                 190
```

```
gcc cga gcg cgg cat att ctg caa gta tgt gaa cat cta cat att ccc      624
Ala Arg Ala Arg His Ile Leu Gln Val Cys Glu His Leu His Ile Pro
        195                 200                 205 gta ccg gaa aaa tta tgc gtg att ggc atc gat aac gaa gaa ctg acc      672
Val Pro Glu Lys Leu Cys Val Ile Gly Ile Asp Asn Glu Glu Leu Thr
    210                 215                 220 cgc tat ctg tcg cgt gtc gcc ctt tct tcg gtc gct cag ggc gcg cgg      720
Arg Tyr Leu Ser Arg Val Ala Leu Ser Ser Val Ala Gln Gly Ala Arg
225                 230                 235                 240 caa atg ggc tat cag gcg gca aaa ctg ttg cat cga tta tta gat aaa      768
Gln Met Gly Tyr Gln Ala Ala Lys Leu Leu His Arg Leu Leu Asp Lys
                245                 250                 255 gaa gaa atg ccg cta cag cga att ttg gtc cca cca gtt cgc gtc att      816
Glu Glu Met Pro Leu Gln Arg Ile Leu Val Pro Pro Val Arg Val Ile
            260                 265                 270 gaa cgg cgc tca aca gat tat cgc tcg ctg acc gat ccc gcc gtt att      864
Glu Arg Arg Ser Thr Asp Tyr Arg Ser Leu Thr Asp Pro Ala Val Ile
        275                 280                 285 cag gcc atg cat tac att cgt aat cac gcc tgt aaa ggg att aaa gtg      912
Gln Ala Met His Tyr Ile Arg Asn His Ala Cys Lys Gly Ile Lys Val
    290                 295                 300 gat cag gta ctg gat gcg gtc ggg atc tcg cgc tcc aat ctt gag aag      960
Asp Gln Val Leu Asp Ala Val Gly Ile Ser Arg Ser Asn Leu Glu Lys
305                 310                 315                 320 cgt ttt aaa gaa gag gtg ggt gaa acc atc cat gcc atg att cat gcc     1008
Arg Phe Lys Glu Glu Val Gly Glu Thr Ile His Ala Met Ile His Ala
                325                 330                 335 gag aag ctg gag aaa gcg cgc agt ctg ctg att tca acc acc ttg tcg     1056
Glu Lys Leu Glu Lys Ala Arg Ser Leu Leu Ile Ser Thr Thr Leu Ser
            340                 345                 350 atc aat gag ata tcg caa atg tgc ggt tat cca tcg ctg caa tat ttc     1104
Ile Asn Glu Ile Ser Gln Met Cys Gly Tyr Pro Ser Leu Gln Tyr Phe
        355                 360                 365 tac tct gtt ttt aaa aaa gca tat gac acg acg cca aaa gag tat cgc     1152
Tyr Ser Val Phe Lys Lys Ala Tyr Asp Thr Thr Pro Lys Glu Tyr Arg
    370                 375                 380 gat gta aat agc gag gtc atg ttg tag                                  1179
Asp Val Asn Ser Glu Val Met Leu
385                 390

<210> SEQ ID NO 12
<211> LENGTH: 392
<212> TYPE: PRT
<213> ORGANISM: Escherichia coli

<400> SEQUENCE: 12

Met Phe Thr Lys Arg His Arg Ile Thr Leu Leu Phe Asn Ala Asn Lys
 1               5                  10                  15

Ala Tyr Asp Arg Gln Val Val Glu Gly Val Gly Glu Tyr Leu Gln Ala
            20                  25                  30

Ser Gln Ser Glu Trp Asp Ile Phe Ile Glu Glu Asp Phe Arg Ala Arg
        35                  40                  45

Ile Asp Lys Ile Lys Asp Trp Leu Gly Asp Gly Val Ile Ala Asp Phe
    50                  55                  60

Asp Asp Lys Gln Ile Glu Gln Ala Leu Ala Asp Val Asp Val Pro Ile
65                  70                  75                  80

Val Gly Val Gly Gly Ser Tyr His Leu Ala Glu Ser Tyr Pro Pro Val
                85                  90                  95

His Tyr Ile Ala Thr Asp Asn Tyr Ala Leu Val Glu Ser Ala Phe Leu
            100                 105                 110
```

His Leu Lys Glu Lys Gly Val Asn Arg Phe Ala Phe Tyr Gly Leu Pro
            115                 120                 125

Glu Ser Ser Gly Lys Arg Trp Ala Thr Glu Arg Glu Tyr Ala Phe Arg
        130                 135                 140

Gln Leu Val Ala Glu Lys Tyr Arg Gly Val Val Tyr Gln Gly Leu
145                 150                 155                 160

Glu Thr Ala Pro Glu Asn Trp Gln His Ala Gln Asn Arg Leu Ala Asp
                165                 170                 175

Trp Leu Gln Thr Leu Pro Pro Gln Thr Gly Ile Ile Ala Val Thr Asp
            180                 185                 190

Ala Arg Ala Arg His Ile Leu Gln Val Cys Glu His Leu His Ile Pro
        195                 200                 205

Val Pro Glu Lys Leu Cys Val Ile Gly Ile Asp Asn Glu Glu Leu Thr
    210                 215                 220

Arg Tyr Leu Ser Arg Val Ala Leu Ser Ser Val Ala Gln Gly Ala Arg
225                 230                 235                 240

Gln Met Gly Tyr Gln Ala Ala Lys Leu Leu His Arg Leu Leu Asp Lys
                245                 250                 255

Glu Glu Met Pro Leu Gln Arg Ile Leu Val Pro Val Arg Val Ile
            260                 265                 270

Glu Arg Arg Ser Thr Asp Tyr Arg Ser Leu Thr Asp Pro Ala Val Ile
        275                 280                 285

Gln Ala Met His Tyr Ile Arg Asn His Ala Cys Lys Gly Ile Lys Val
    290                 295                 300

Asp Gln Val Leu Asp Ala Val Gly Ile Ser Arg Ser Asn Leu Glu Lys
305                 310                 315                 320

Arg Phe Lys Glu Glu Val Gly Glu Thr Ile His Ala Met Ile His Ala
                325                 330                 335

Glu Lys Leu Glu Lys Ala Arg Ser Leu Leu Ile Ser Thr Thr Leu Ser
            340                 345                 350

Ile Asn Glu Ile Ser Gln Met Cys Gly Tyr Pro Ser Leu Gln Tyr Phe
        355                 360                 365

Tyr Ser Val Phe Lys Lys Ala Tyr Asp Thr Thr Pro Lys Glu Tyr Arg
    370                 375                 380

Asp Val Asn Ser Glu Val Met Leu
385                 390

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 13
ggcaactatg catatcttcg cgc                                          23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 14
gcgtgaatga attggcttag gtgg                                         24

```
<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 15
cagacagcga gcgaggatcg c                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 16
tgtgcggtta tccatcgctg c                                              21
```